(12) United States Patent
Nguyen et al.

(10) Patent No.: US 7,749,365 B2
(45) Date of Patent: Jul. 6, 2010

(54) OPTIMIZED SAMPLE INJECTION STRUCTURES IN MICROFLUIDIC SEPARATIONS

(75) Inventors: Michael Nguyen, San Jose, CA (US); Luc Bousse, Los Altos, CA (US)

(73) Assignee: IntegenX, Inc., Pleasanton, CA (US)

( * ) Notice: Subject to any disclaimer, the term of this patent is extended or adjusted under 35 U.S.C. 154(b) by 999 days.

(21) Appl. No.: 11/460,236

(22) Filed: Jul. 26, 2006

(65) Prior Publication Data

US 2007/0175756 A1    Aug. 2, 2007

Related U.S. Application Data

(60) Provisional application No. 60/764,393, filed on Feb. 1, 2006.

(51) Int. Cl.
G01N 27/26 (2006.01)
B81B 7/00 (2006.01)

(52) U.S. Cl. .................... 204/453; 204/604; 422/82; 436/180

(58) Field of Classification Search ............ 204/451, 204/601, 604, 453; 422/81, 82, 103, 99, 422/100; 137/834, 251.1, 247, 330; 251/129.03; 436/174, 180, 53
See application file for complete search history.

(56) References Cited

U.S. PATENT DOCUMENTS

| | | |
|---|---|---|
| 3,352,643 A | 11/1967 | Ando et al. |
| 3,433,257 A | 3/1969 | Jensen |
| 3,568,692 A | 3/1971 | Metzger et al. |
| 5,376,252 A | 12/1994 | Ekström et al. |
| 5,453,163 A | 9/1995 | Yan |
| 5,571,410 A | 11/1996 | Swedberg et al. |
| 5,587,128 A | 12/1996 | Wilding et al. |
| 5,705,813 A | 1/1998 | Apffel et al. |
| 5,741,462 A | 4/1998 | Nova et al. |
| 5,750,015 A | 5/1998 | Soane et al. |
| 5,770,029 A | 6/1998 | Nelson et al. |
| 5,775,371 A | 7/1998 | Pan et al. |

(Continued)

FOREIGN PATENT DOCUMENTS

EP    0527905 B1    11/1995

(Continued)

OTHER PUBLICATIONS

Jacobson, S. C., and J. M. Ramsey, "Electrokinetic Focusing in Microfabricated Channel Structures", Analytical Chemistry, vol. 69, No. 16, Aug. 15, 1997, p. 3212-3217.*

(Continued)

*Primary Examiner*—Alex Noguerola
*Assistant Examiner*—J. Christopher Ball
(74) *Attorney, Agent, or Firm*—Wilson Sonsini Goodrich & Rosati; John Storella

(57) ABSTRACT

The invention herein provides improved sample injection systems and related methods to create microfluidic devices with symmetrical channel configurations that can produce relatively large sample volumes. An embodiment of the invention provides microfluidic structures with different geometries that are symmetrical from the perspective of a sample load channel and a sample waste channel, which essentially eliminates issues of time offset and other problems commonly associated with twin-T sample formation techniques. A split-injection approach and related methods of sample plug formation are therefore provided.

20 Claims, 12 Drawing Sheets

U.S. PATENT DOCUMENTS

| | | | |
|---|---|---|---|
| 5,856,174 A | 1/1999 | Lipshutz et al. |
| 5,863,502 A | 1/1999 | Southgate et al. |
| 5,908,552 A | 6/1999 | Dittmann et al. |
| 5,922,591 A | 7/1999 | Anderson et al. |
| 5,942,443 A | 8/1999 | Parce et al. |
| 5,971,158 A | 10/1999 | Yager et al. |
| 6,001,229 A | 12/1999 | Ramsey |
| 6,007,690 A | 12/1999 | Nelson et al. |
| 6,007,775 A | 12/1999 | Yager |
| 6,010,607 A | 1/2000 | Ramsey |
| 6,048,100 A | 4/2000 | Thrall et al. |
| 6,073,482 A | 6/2000 | Moles |
| 6,103,199 A | 8/2000 | Bjornson et al. |
| 6,120,184 A | 9/2000 | Laurence et al. |
| 6,136,212 A | 10/2000 | Mastrangelo et al. |
| 6,168,948 B1 | 1/2001 | Anderson et al. |
| 6,176,962 B1 | 1/2001 | Soane et al. |
| 6,190,616 B1 | 2/2001 | Jovanovich et al. |
| 6,207,031 B1 | 3/2001 | Adourian et al. |
| 6,235,471 B1 | 5/2001 | Knapp et al. |
| 6,280,589 B1 | 8/2001 | Manz et al. |
| 6,319,476 B1 | 11/2001 | Victor, Jr. et al. |
| 6,322,683 B1 | 11/2001 | Wolk et al. |
| 6,379,929 B1 | 4/2002 | Burns et al. |
| 6,403,338 B1 | 6/2002 | Knapp et al. |
| 6,408,878 B2 | 6/2002 | Unger et al. |
| 6,423,536 B1 | 7/2002 | Jovanovich et al. |
| 6,432,290 B1 | 8/2002 | Harrison et al. |
| 6,454,924 B2 | 9/2002 | Jedrzejewski et al. |
| 6,489,112 B1 | 12/2002 | Hadd et al. |
| 6,521,188 B1 | 2/2003 | Webster |
| 6,524,456 B1 | 2/2003 | Ramsey et al. |
| 6,532,997 B1 | 3/2003 | Bedingham et al. |
| 6,533,914 B1 | 3/2003 | Liu |
| 6,537,757 B1 | 3/2003 | Langmore et al. |
| 6,544,734 B1 | 4/2003 | Briscoe et al. |
| 6,551,839 B2 | 4/2003 | Jovanovich et al. |
| 6,581,441 B1 | 6/2003 | Paul |
| 6,605,454 B2 | 8/2003 | Barenburg et al. |
| 6,613,525 B2 | 9/2003 | Nelson et al. |
| 6,614,228 B2 | 9/2003 | Hofmann et al. |
| 6,618,679 B2 | 9/2003 | Loehrlein |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |
| 6,632,655 B1 | 10/2003 | Mehta et al. |
| 6,663,833 B1 | 12/2003 | Stave et al. |
| 6,685,442 B2 | 2/2004 | Chinn et al. |
| 6,752,922 B2 | 6/2004 | Huang et al. |
| 6,764,648 B1 | 7/2004 | Roach et al. |
| 6,782,746 B1 | 8/2004 | Hasselbrink et al. |
| 6,786,708 B2 | 9/2004 | Brown et al. |
| 6,787,111 B2 | 9/2004 | Roach et al. |
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,824,663 B1 | 11/2004 | Boone |
| 6,829,753 B2 | 12/2004 | Lee et al. |
| 6,852,287 B2 | 2/2005 | Ganesan |
| 6,870,185 B2 | 3/2005 | Roach et al. |
| 6,885,982 B2 | 4/2005 | Harris et al. |
| 6,899,137 B2 | 5/2005 | Unger et al. |
| 6,923,907 B2 | 8/2005 | Hobbs et al. |
| 6,929,030 B2 | 8/2005 | Unger et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 7,005,493 B2 | 2/2006 | Huang et al. |
| 7,015,030 B1 | 3/2006 | Fouillet et al. |
| 7,198,759 B2 | 4/2007 | Bryning et al. |
| 7,312,611 B1 | 12/2007 | Harrison et al. |
| 7,323,305 B2 | 1/2008 | Leamon et al. |
| 7,438,856 B2 | 10/2008 | Jedrzejewski et al. |
| 7,445,926 B2 | 11/2008 | Mathies et al. |
| 7,488,603 B2 | 2/2009 | Gjerde et al. |
| 2002/0022587 A1 | 2/2002 | Ferguson et al. |
| 2002/0047003 A1 | 4/2002 | Bedingham et al. |
| 2002/0048536 A1 | 4/2002 | Bergh et al. |
| 2002/0051992 A1 | 5/2002 | Bridgham et al. |
| 2002/0058332 A1 | 5/2002 | Quake et al. |
| 2002/0098097 A1 | 7/2002 | Singh |
| 2002/0110900 A1 | 8/2002 | Jovanovich et al. |
| 2002/0119480 A1 | 8/2002 | Weir et al. |
| 2002/0119482 A1 | 8/2002 | Nelson et al. |
| 2003/0217923 A1 | 11/2003 | Harrison et al. |
| 2004/0014091 A1 | 1/2004 | Duck et al. |
| 2004/0037739 A1 | 2/2004 | Mcneely et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0086872 A1 | 5/2004 | Childers et al. |
| 2004/0132170 A1 | 7/2004 | Storek et al. |
| 2004/0151629 A1 | 8/2004 | Pease et al. |
| 2004/0197845 A1 | 10/2004 | Hassibi et al. |
| 2004/0209354 A1 | 10/2004 | Mathies et al. |
| 2004/0224380 A1 | 11/2004 | Chou et al. |
| 2005/0047967 A1 | 3/2005 | Chuang et al. |
| 2005/0053952 A1 | 3/2005 | Hong et al. |
| 2005/0161326 A1 | 7/2005 | Morita et al. |
| 2005/0224134 A1 | 10/2005 | Yin et al. |
| 2005/0224352 A1 | 10/2005 | Harrison et al. |
| 2005/0255003 A1 | 11/2005 | Summersgill et al. |
| 2005/0287572 A1 | 12/2005 | Mathies et al. |
| 2006/0027456 A1 | 2/2006 | Harrison et al. |
| 2006/0057209 A1 | 3/2006 | Chapman et al. |
| 2006/0073484 A1 | 4/2006 | Mathies et al. |
| 2006/0076068 A1 | 4/2006 | Young et al. |
| 2006/0163143 A1 | 7/2006 | Chirica et al. |
| 2006/0186043 A1 | 8/2006 | Covey et al. |
| 2006/0266645 A1 | 11/2006 | Chen et al. |
| 2007/0017812 A1 | 1/2007 | Bousse |
| 2007/0237686 A1 | 10/2007 | Mathies et al. |
| 2007/0248958 A1 | 10/2007 | Jovanovich et al. |
| 2007/0297947 A1 | 12/2007 | Sommers et al. |
| 2008/0014576 A1 | 1/2008 | Jovanovich et al. |
| 2008/0237146 A1 | 10/2008 | Harrison et al. |
| 2009/0035770 A1 | 2/2009 | Mathies et al. |
| 2009/0060797 A1 | 3/2009 | Mathies et al. |
| 2009/0084679 A1 | 4/2009 | Harrison et al. |

FOREIGN PATENT DOCUMENTS

| | | |
|---|---|---|
| EP | 1065378 B1 | 4/2002 |
| JP | 408327594 A | 12/1996 |
| WO | WO 96/04547 A1 | 2/1996 |
| WO | WO 98/52691 A1 | 11/1998 |
| WO | WO 99/36766 A1 | 7/1999 |
| WO | WO 99/40174 A1 | 8/1999 |
| WO | WO 00/40712 A1 | 7/2000 |
| WO | WO 00/60362 A1 | 10/2000 |
| WO | WO 01/38865 A1 | 5/2001 |
| WO | WO 01/85341 A1 | 11/2001 |
| WO | WO 02/043615 A2 | 6/2002 |
| WO | WO 02/043615 A3 | 3/2003 |
| WO | WO 2004/098757 A2 | 11/2004 |
| WO | WO 2005/075081 A1 | 8/2005 |
| WO | WO 2004/098757 A3 | 5/2006 |

OTHER PUBLICATIONS

Amendment and Request for Correction of Inventorship mailed Jan. 10, 2008 in U.S. Appl. No. 10/750,533.

Anderson, et al. A miniature integrated device for automated multistep genetic assays. Nucleic Acids Research. 2000;28:e60.

Bings, et al. Microfluidic Devices Connected to Fused-Silica Capillaries with Minimal Dead Dead Volume. Analytical Chemistry. 1999;71(15):3292-3296.
Blazej, et al. Microfabricated bioprocessor for integrated nanoliter-scale Sanger DNA sequencing. Proc. Natl. Acad. Sci. USA 2006;103:7240-7245.
Blazej, et al. Polymorphism Ratio Sequencing: A New Approach for Single Nucleotide Polymorphism Discovery and Genotyping. Genome Research. 2003;13:287-293.
Brenner, et al. Gene expression analysis by massively parallel signature sequencing (MPSS) on microbead arrays. Nature Biotechnology. 2000;18(6):630-634.
Buchholz, et al. The use of light scattering for precise characterization of polymers for DNA sequencing by capillary electrophoresis. Electrophoresis. 2001;22:4118-4128.
CAPLUS abstract of Krohkin et al. Modified silica as a stationary phase for ion chromatography. Journal of Chromatography A. 1995;706:93-8.
Chan, et al. Microfabricated Polymer Devices for Automated Sample Delivery of Peptides for Analysis by Electrospray Ionization Tandem Mass Spectrometry. Analytical Chemistry. 1999;71(20):4437-4444.
Chiem, et al. Microchip systems for immunoassay: an integrated immunoreactor with electrophoretic separation for serum theophylline determination. Clinical Chemistry. 1998;44(3):591-598.
Chiem, et al. Room temperature bonding of micromachined glass devices for capillary electrophoresis. Sensors and Actuators. 2000;B63(3):147-152.
Coleman, et al. A sequential injection microfluidic mixing strategy. Microfluidics and Nanofluidics. 2005;319-327.
Curcio, et al. Continuous Segmented-Flow Polymerase Chain Reaction for High-Throughput Miniaturized DNA Amplification. Analytical Chemistry. 2003;75(1):1-7.
Diehl, et al. BEAMing: single-molecule PCR on microparticles in water-in-oil emulsions. Nature Methods. 2006;3(7):551-9.
Doherty, et al. Sparsely Cross-linked "Nanogel" Matrices as Fluid, Mechanically Stablized Polymer Networks for High-Throughput Microchannel DNA Sequencing. Analytical Chemistry. 2004;76:5249-5256.
Doherty, et al. Sparsely cross-linked "nanogels" for microchannel DNA sequencing. Electrophoresis. 2003;24(24):4170-4180.
Dorfman, et al. Contamination-Free Continuous Flow Microfluidic Polymerase Chain Reaction for Quantitative and Clinical Applications. Analytical Chemistry. 2005;77(11):3700-3704.
Doyle, et al. Self-Assembled Magnetic Matrices for DNA Separation Chips. Science. 2000;295:2237.
Dressman, et al. Transforming single DNA molecules into fluorescent magnetic particles for detection and enumeration of genetic variations. Proc Natl Acad Sci USA. 2003;100(15):8817-8822.
Emrich, et al. Microfabricated 384-Lane Capillary Array Electrophoresis Bioanalyzer for Ultrahigh-Throughput Genetic Analysis. Analytical Chemistry. 2002;74(19):5076-5083.
Ericson, et al. Electroosmosis- and Pressure-Driven Chromatography in Chips Using Continuous Beds. Analytical Chemistry. 2000;72(1):81-87.
Ewing, et al. Base-Calling of Automated Sequencer Traces Using Phred. I. Accuracy Assessment. Genome Research. 1998;8:175-185.
Ewing, et al. Base-Calling of Automated Sequencer Traces Using Phred. II. Error probabilities. Genome Research. 1998;8:186-194.
Figeys, et al. A Microfabricated Device for Rapid Protein Identification by Microelectrospray Ion Trap Mass Spectrometry. Analytical Chemistry. 1997;69(16):3153-3160.
Figeys, et al. An Integrated Microfluidics-Tandem Mass Spectrometry System for Automated Protein Analysis. Analytical Chemistry. 1998;70(18):3728-3734.
Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications In Mass Spectrometry. 1998;12:1435-1444.
Figeys, et al. Nanoflow Solvent Gradient Delivery from a Microfabricated Device for Protein Identifications by Electrospray Ionization Mass Spectrometry. Analytical Chemistry. 1998;70(18):3721-3727.
Francis, et al. Flow analysis based on a pulsed flow of solution: theory, instrumentation and applications. Talanta. 2002;58(6):1029-1042.
Ghadessy, et al. Directed evolution of polymerase function by compartmentalized self-replication. Proc Natl Acad Sci USA. 2001;98:4552-4557.
Giddings, et al. A software system for data analysis in automated DNA sequencing. Genome Research. 1998;8:644-665.
Goll, et al. Microvalves with bistable buckled polymer diaphragms. Journal of Micromechanics and Microengineering. 1996;6:77-79.
Grover, et al. An integrated microfluidic processor for single nucleotide polymorphism-based DNA computing. Lab on a Chip. 2005;5(10):1033-1040.
Grover, et al. Development and multiplexed control of latching pneumatic valves using microfluidic logical structures. Lab on a chip. 2006;6:623-631.
Grover, et al. Monolithic membrane valves and diaphragm pumps for practical large-scale integration into glass microfluidic devices. Sensors and Actuators. 2003;B89:315-323.
Grover, et al. Practical Valves and Pumps for Large-Scale Integration into Microfludic Analysis Devices. Micro Total Analysis Systems. 2002;1:136-138.
Hansen, et al. A robust and scalable microfluidic metering method that allows protein crystal growth by free interface diffusion. Proc Natl Acad Sci USA. 2002;99(26):16531-16536.
Harrison, et al. Micromachining a Miniaturized Capillary Electrophoresis-Based Chemical Analysis System on a Chip. Science. 1993;261(5123):895-897.
Hayes, et al. EDGE: A Centralized Resource for the Comparison, Analysis, and Distribution of Toxicogenomic Information. Molecular Pharmacology. 2005;67(4):1360-1368.
Hultman, et al. Bidirectional Solid-Phase Sequencing of In Vitro-Amplified Plasmid DNA. BioTechniques. 1991;10(1):84-93.
International Preliminary Report for corresponding PCT Application No. PCT/CA2000/01421 dated Feb. 14, 2002.
International Preliminary Report for corresponding PCT Application No. PCT/US2005/018678 dated Nov. 13, 2007.
International Preliminary Report for corresponding PCT Application No. PCT/US2005/033347 dated Mar. 20, 2007.
International Preliminary Report for corresponding PCT Application No. PCT/US2007/007381 dated Sep. 23, 2008.
International Preliminary Report for corresponding PCT Application No. PCT/US2007/02721 dated Aug. 5, 2008.
International Preliminary Report for corresponding PCT Application No. PCT/US2007/061573 dated Aug. 26, 2008.
International Search Report for PCT/US2005/033347.
Ju, et al. Fluorescence energy transfer dye-labeled primers for DNA sequencing and analysis. Proc. Natl. Acad. Sci. USA. 1995;92:4347-4351.
Kan, et al. A novel thermogelling matrix for microchannel DNA sequencing based on poly-N-alkoxyalkylaclylamide copolymers. Electrophoresis. 2003;24(24):4161-4169.
Koh, et al. Integrating Polymerase Chain Reaction, Valving, and Electrophoresis in a Plastic Device for Bacterial Detection. Analytical Chemistry. 2003;75(17):4591-4598.
Kopp, et al. Chemical Amplification Continuous-Flow PCR on a Chip. Science. 1998;280:1046-1048.
Lagally, et al. Fully integrated PCR-capillary electrophoresis microsystem for DNA analysis. Lab on a Chip. 2001;1(2):102-107.
Lagally, et al. Integrated Portable Genetic Analysis Microsystem for Pathogen/Infectious Disease Detection. Analytical Chemistry. 2004;76:3162-3170.
Lagally, et al. Monolithic integrated microfluidic DNA amplification and capillary electrophoresis analysis system. Sensors and Actuators. 2000;B63(3):138-146.
Lagally, et al. Single-Molecule DNA Amplification and Analysis in an Integrated Microfluidic Device. Analytical Chemistry. 2001;73(3): 565-570.
Lazar, et al. Subattomole-Sensitivity Microchip Nanoelectrospray Source with Time-of-Flight Mass Spectrometry Detection. Analytical Chemistry. 1999;71(17):3627-3631.
Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.

Li, et al. Rapid and sensitive separation of trace level protein digests using microfabricated devices coupled to a quadrupole—time-of-flight mass spectrometer. Electrophoresis. 2000;21:198-210.

Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.

Licklider, et al. A Micromachined Chip-Based Electrospray Source for Mass Spectrometry. Analytical Chemistry. 2000;72(2):367-375.

Lisec, et al. A bistable pneumatic microswitch for driving fluidic components. Sensors and Actuators. 1996;A54:746-749.

Liu, et al. Automated parallel DNA sequencing on multiple channel microchips. Proc. Natl. Acad. Sci. USA. 2000;97(10):5369-5374.

Liu, et al. Optimization of High-Speed DNA Sequencing on Microfabricated Capillary Electrophoresis Channels. Analytical Chemistry. 1999;71:566-573.

Margulies, et al. Genome sequencing in microfabricated high-density picolitre reactors. Nature. 2005;437(7057):376-80. (Abstact only).

Melin, et al. A Passive 2-Dimensional Liquid Sample Micromixer. 7th International Conference on Miniaturized Chemical and Biochemical Analysis Systems. 2003;167-170.

Mitra, et al. Digital genotyping and haplotyping with polymerase colonies. Proc Natl Acad Sci USA. 2003.100(10):15926-5931.

Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.

Ocvirk, et al. High Performance Liquid Chromatography Partially Integrated onto a Silicon Chip. Analytical Methods and Instrumentation. 1995;2:74-82.

Ocvirk, et al. Optimization of confocal epifluorescence microscopy for microchip-based miniaturized total analysis systems. The Analyst. 1998;123:1429-1434.

Office Action Final dated Feb. 19, 2008 issued in U.S. Appl. No. 10/540,658.

Office Action Final dated Feb. 6, 2008 issued in U.S. Appl. No. 11/139,018.

Office Action mailed Apr. 27, 2007 in U.S. Appl. No. 11/139,018, filed May 25, 2005.

Office Action mailed Jul. 2, 2007 in U.S. Appl. No. 10/540,658, filed Jun. 23, 2005.

Office Action mailed Jul. 12, 2007 in U.S. Appl. No. 10/750,533, filed Dec. 29, 2003.

Ohori, et al. Partly disposable three-way mirovalve for a medical micro total analysis system (muTAS). Sensors and Actuators. 1998;A64(1): 57-62.

Oleschuk, et al. Trapping of Bead-Based Reagents within Microfluidic Systems: On-Chip Solid-Phase Extraction and Electrochromatography. Analytical Chemistry. 2000;72:585-590.

Olsen, et al. Immobilization of DNA Hydrogel Plugs In Microfluidic Channels. Analytical Chemistry. 2002;74:1436-1441.

Paegel, et al. High-throughput DNA sequencing with a 96-lane capillary array electrophoresis bioprocessor. Proc Natl Acad Sci USA. 2002;99:574-579.

Paegel, et al. Microchip Bioprocessor for Integrated Nanovolume Sample Purification and DNA Sequencing. Analytical Chemistry. 2002;74(19):5092-5098.

Paegel, et al. Microfluidic devices for DNA sequencing: sample preparation and electrophoretic analysis. Current Opinion in Biotechnology. 2003;14(1):42-50.

Paegel, et al. Turn Geometry for Minimizing Band Broadening in Microfabricated Capillary Electrophoresis Channels. Analytical Chemistry. 2000;72:3030-3037.

PCT Notification of Transmittal of the International Search Report and The Written Opinion of the International Searching Authority, or the Declaration, mailed Jun. 17, 2008, Application No. PCT/US2007/082568 (UCALP067WO).

Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.

Ramsey, et al. Generating Electrospray from Microchip Devices Using Electroosmotic Pumping. Analytical Chemistry. 1997;69(6):1174-1178.

Rohr, et al. Porous polymer monoliths: Simple and efficient mixers prepared by direct polymerization in the channels of microfluidic chips. Electrophoresis. 2001;22:3959-3967.

Rye, et al. High-sensitivity two-color detection of double-stranded DNA with a confocal fluorescence gel scanner using ethidium homodimer and thiazole orange. Nucleic Acids Research. 1991;19(2):327-333.

Scherer, et al. High-Pressure Gel Loader for Capillary Array Electrophoresis Microchannel Plates. Biotechniques. 2001;31(5):1150-1154.

Schomburg, et al. Design Optimization of Bistable Microdiaphragm Valves. Sensors and Actuators. 1998;A64:259-264.

Seifar, et al. Capillary electrochromatography with 1.8-mum ODS-modified porous silica particles. Journal of Chromatography. 1998; A808:71-77.

Simpson, et al. High-throughput genetic analysis using microfabricated 96-sample capillary array electrophoresis microplates. Proc Natl Acad Sci USA. 1998;95:2256-2261.

Simpson, et al. Microfabrication Technology for the Production of Capillary Array Electrophoresis Chips. Biomedical Microdevices. 1998;1:7-26.

Soper, et al. Sanger DNA Sequencing Reactions Performed in a Solid-Phase Nanoreactor Directly Coupled to Capillary Gel Electrophoresis. Analytical Chemistry. 1998;70:4036-4043.

Spiering, et al. Novel microstructures and technologies applied in chemical analysis techniques. 1997 International Conference on Solid-State Sensors and Actuators. 1997;1:511-514.

Takao, et al. A Pneumatically Actuated Full In-Channel Microvalve With MOSFET-Like Function in Fluid Channel Networks. Journal of Microelectromechanical Systems. 2002;11(5):421-426.

Takao, et al. Microfluidic Integrated Circuits for Signal Processing Using Analogous Relationship Betweeen Pneumatic Microvalve and MOSFET. Journal of Microelectromechanical Systems. 2003;12(4):497-505.

Thomas, et al. Application of Genomics to Toxicology Research. Environmental Health Perspectives. 2002;110(6):919-923.

Thorsen, et al. Microfluidic Large-Scale Integration. Science. 2002;298(5593):580-584.

Tice, et al. Formation of Droplets and Mixing in Multiphase Microfluidics at Low Values of the Reynolds and the Capillary Numbers. Langmuir. 2003;19:9127-9133.

Unger, et al. Monolithic Microfabricated Valves and Pumps by Multilayer Soft Lithography. Science. 2000;288:113-116.

Van Der Moolen, et al. A Micromachined Injection Device for CZE: Application to Correlation CZE. Analytical Chemistry. 1997;69(20):4220-4225.

Van Der Moolen, et al. Correlation Capillary Zone Electrophoresis, a Novel Technique to Decrease Detection Limits. Chromatographia. 1995;40(7/8):368-374.

Vazquez, et al. Electrophoretic Injection within Microdevices. Analytical Chemistry. 2002;74:1952-1961.

Veenstra, et al. The design of an in-plane compliance structure for microfluidical systems. Sensors and Actuators. 2002;B81:377-383.

Waller, et al. Quantitative Immunocapture PCR Assay for Detection of *Campylobacter jejuni* in Foods. Applied Environmental Microbiology. 2000; 66(9):4115-4118.

Weimer, et al. Solid-Phase Capture of Proteins, Spores, and Bacteria. Applied Environmental Microbiology. 2001;67(3):1300-1307.

Wen, et al. Microfabricated isoelectric focusing device for direct electrospray ionization-mass spectrometry. Electrophoresis. 2000;21:191-197.

Williams, et al. Amplification of complex gene libraries by emulsion PCR. Nature Methods. 2006;3(7):545-50.

Woolley, et al. Functional Integration of PCR Amplification and Capillary Electrophoresis in a Microfabricated DNA Analysis Device. Analytical Chemistry. 1996;68(23):4081-4086.

Wright, et al. Behavior and Use of Nonaqueous Media without Supporting Electrolyte in Capillary Electrophoresis and Capillary Electrochromatography. Analytical Chemistry. 1997;69(16):3251-3259.

Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.

Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.

Xue, et al. Multichannel Microchip Electrospray Mass Spectrometry. Analytical Chemistry. 1997;69(3):426-430.

Yang, et al. A MEMS thermopneumatic silicone rubber membrane valve. Sensors and Actuators. 1998;A64(1):101-108.

Yu, et al. Preparation of Monolithic Polymers with Controlled Porous Properties for Microfluidic Chip Applications Using Photoinitiated Free Radial Polymerization. Journal of Polymer Science. 2002;40:755-769.

Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.

Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.

Zhang, et al. Microfabricated Devices for Capillary Electrophoresis-Electrospray Mass Spectrometry. Analytical Chemistry. 1999;71(15):3258-3264.

Wikipedia brochure for defining stocahstic process. Sep. 2, 2009.

* cited by examiner (a)

(b)

OPTIMIZED SAMPLE INJECTION STRUCTURES IN MICROFLUIDIC SEPARATIONS

CROSS-REFERENCE

This application claims the benefit of U.S. Provisional Application No. 60/764,393, filed Feb. 1, 2006, which is incorporated herein by reference in its entirety.

FIELD OF THE INVENTION

The invention relates to sample introduction techniques and apparatus for microfluidic systems. More particularly, the invention relates to improved sample injection structures and methods for defining accurate volumes of material for microfluidic separations.

BACKGROUND OF THE INVENTION

Miniaturization is the recent trend in analytical chemistry and life sciences. In the past two decades, miniaturization of fluid handling and fluid analysis has been emerging in the interdisciplinary research field of microfluidics. Microfluidic applications cover micro arrays, DNA sequencing, sample preparation and analysis, cell separation and detection, as well environmental monitoring. The use of microfluidics principles for these applications attracts interest from both industry and academia. Some of the benefits achieved to date include the required use of only small amounts of sample and reagent, less time consuming procedures at a lower cost and higher throughput.

New microtechnologies and components have often been driven by the pharmaceutical industry's demand for high quality medicines produced at a rapid rate and a lower cost. In (bio)chemical and biological applications, miniaturization offers a solution to several challenges including increasing throughput, allowing automation, and decreasing costs by reducing the amount of expensive reagents used. In addition, miniaturization promises higher selectivity, higher yield, fewer byproducts, efficient heat management, and increased process safety.

Numerous designs are known for performing these microfluidic operations in conjunction with particular protocols. For example, by applying appropriate voltage gradients, a sample volume in which certain ions of interest reside can be delineated within a small volume, often referred to as a plug. This operation is important in separation techniques such as capillary electrophoresis (CE) in order to attain a high concentration of sample components to be detected in a sample plug, with minimal loss of sample within the volume preceding or following the plug. There is a need for improved sample formation procedures and microfluidic apparatus that can provide sharply delineated volumes of material for analysis and separation of its components.

INCORPORATION BY REFERENCE

All publications, patents and patent applications mentioned in this specification are herein incorporated by reference to the same extent as if each was specifically and individually indicated to be incorporated by reference.

SUMMARY OF INVENTION

The invention provides improved sample injection systems and related methods of utilizing microfluidic devices with channel layouts that can produce relatively large and well defined sample volumes. The various designs and methodologies provided herein in accordance with the invention do not suffer from the same disadvantages associated with previous approaches relying on confined channel geometries such as the problem of time offset with a twin-T configuration. In accordance with an aspect of the invention, microfluidic structures are formed with a sample channel geometry that is symmetrical from the perspective of a sample load channel and a substantially aligned sample waste channel, which essentially eliminates issues of time offset and its associated problems. For example, a sample channel may be formed leading from a supply reservoir to a waste or a drain-reservoir on a microfluidic device. A separation channel to which a sample volume is delivered may intersect the sample channel at a desired location, preferably at a perpendicular position relative to the sample channel. On either side of this intersection, the device may include two buffer channels each formed on either side of the separation channel. Each buffer channel preferably intersects the sample channel at a point equidistant from a separation channel. Accordingly, a well defined sample volume may be formed in the region within the sample channel between the pair of buffer channels to provide "split-injection" of a sample into the separation channel. Other embodiments of the invention may be adapted for other applications involving formation a sample plug by split injection other than separation processes.

A preferable embodiment provides microstructures that can perform loading of more defined sample volumes of relatively increased size in comparison to plugs formed using convention twin-T procedures and devices. These volumes can be formed regardless of the mobility of the sample components. These may include a microfluidic sample region that is distinctly formed from a microfluidic channel portion having a defined length and cross-sectional area (sample volume). The microfluidic channel portion can be also formed with variable x-y dimensions laterally (two dimensions) in the plane of the device, and possibly also with variable depth z dimensions (three dimensions). Various implementations of sample formation techniques and apparatus in accordance with this aspect of the invention are described herein.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

Figure 1:
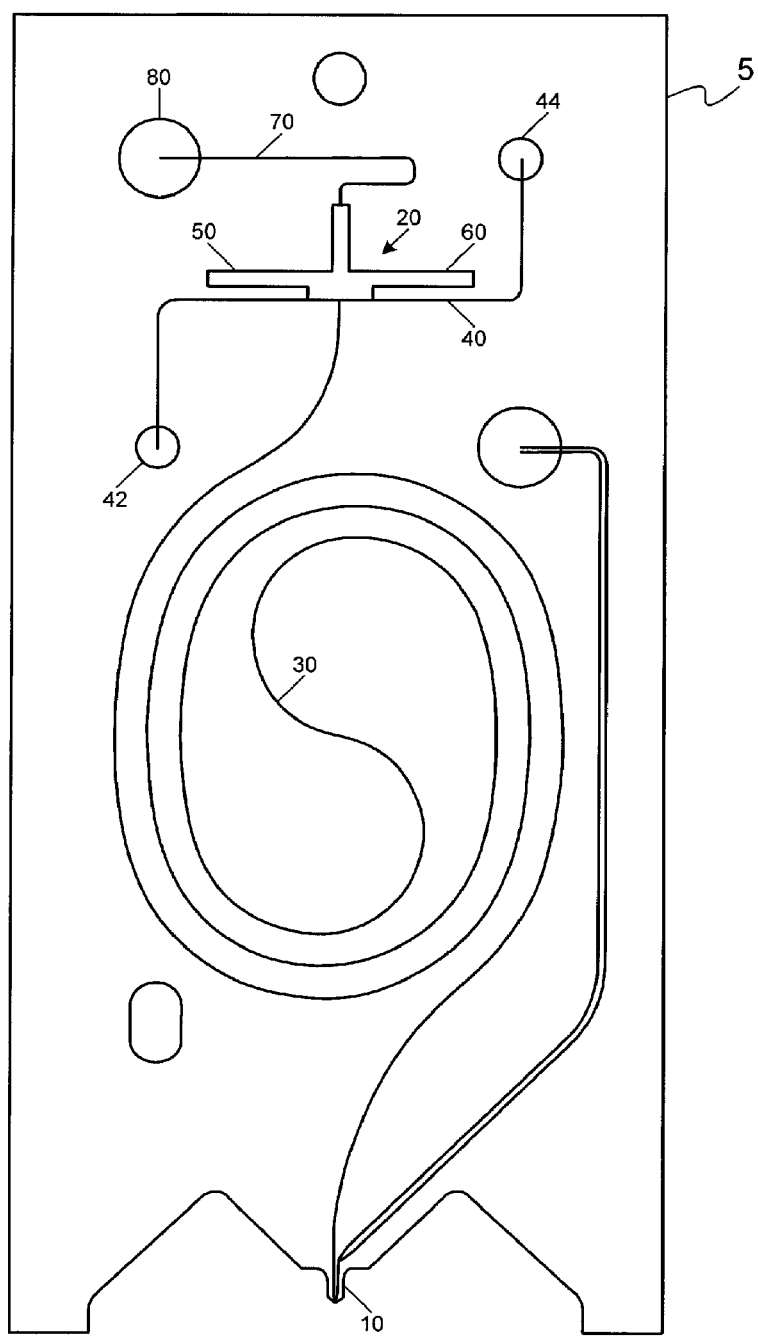
FIG. 1 illustrates a top view of a chip with split injector for introducing a sample into a separation channel.

The illustrations included within this specification describe many of the advantages, and features of the invention. It shall be understood that similar reference numerals and characters noted within the illustrations herein may designate the same or like features of the invention. The illustrations and features depicted herein are not necessarily drawn to scale.

DESCRIPTION OF THE INVENTION

The term "sample" used herein, includes but not limited to, a biomaterial such as by way of example only, a protein such as an enzyme or a synthetic polypeptide, or it can be a nucleic acid such as RNA or DNA or an organic or inorganic small molecule. A biomaterial that is a macromolecule may comprise all or a portion of a nucleic acid or a protein. The protein or polypeptide may comprise an epitope, an antibody, an antibody fragment, an enzyme, or any other embodiment of a molecule containing peptide bonds. A biomaterial can be hormone, for example, the hormone may be a steroid for example, a sex steroid or a glucocorticoid, or a polypeptide hormone such as a cytokine. The sample may comprise all or a portion of an antibody or an antigenic material, or all or a portion of an enzyme. The sample may include blood, body fluids including amniotic fluid, cerebrospinal, pleural, peri- cardial, peritoneal, seminal and synovial fluid, in addition to blood, sweat, saliva, urine and tears, and tissue samples, and excreta, and environmental and industrial substances (including atmospheric gases, water and aqueous solutions, industrial chemicals, and soils). The sample may also include buffers, drugs and various other chemical compounds, such as linkers, by way of example only, dithiobis(succinimidyl-undecanoate) (DSU), long chain succinimido-6[3-(2-pyridyldithio)propionamido]hexanoate (LCSPDP), which contains pyridyldithio and NHS ester reactive groups that react with sulfhydryl and amino groups, succinimidyl-6[3-(2-pyridyldithio)-propionamido]hexanoate (SPDP), which contains pyridyldithio and NHS ester reactive groups that react with sulfhydryl and amino groups, and m-maleimidobenzoyl-N-hydroxysuccinimide ester (MBS), which contains NHS ester and maleimide reactive groups that react with amino and sulfhydryl groups.

Microfluidic devices and structures have been used for electrokinetic sample movement, and electrokinetic separations (see U.S. Pat. No. 6,280,589 entitled, Method for Controlling Sample Introduction in Microcolumn Separation Techniques and Sample Device, incorporated by reference herein it its entirety). It has been demonstrated that the ability of such microfluidic devices to perform separations is much faster than conventional capillary electrophoresis using fused silica capillaries. This increase in speed is due to the ability of a microfluidic device to define the sample plug to be separated very accurately. A method has been demonstrated to define a picoliter-sized sample plug by confining it at the intersection of two channels by electrical fields in all channel branches (see U.S. Pat. No. 6,010,607 entitled Apparatus and Method for Performing Microfluidic Manipulations for Chemical Analysis and Synthesis, incorporated by reference herein it its entirety). Thus, a critical component of a microfluidic separation system is the intersection or intersections that define the sample plug that will be separated, together with the method of applying electrical fields as a function of time to create a sample plug.

FIG. 1 illustrates a top view of a microfluidic chip 5 provided in accordance with an aspect of the invention that is formed with a recessed tip 10, a split injector 20, and an "all curved" separation channel 30. The all curved separation channel 30 is formed without or substantially without linear channel sections (straightaways) along a portion of the device 5. This exemplary embodiment of the invention provides a microfluidic chip that supports electrophoretic separation. A separation channel 30 may be included having a serpentine configuration leading to the recessed tip 10 portion at which sample and/or selected buffers or other solutions are sprayed off the chip 5. In addition, the chip 5 may include a sample channel 40 fluidly connected to a sample supply reservoir 42 and a sample waster reservoir 44. The separation channel 30 may intersect the sample channel 40 and form a T-intersection wherein the separation channel is perpendicular to sample channel. A pair of buffer channels 50 and 60 may be formed on either side of the intersection. The buffer channels 50 and 60 may be formed of various lengths and lead to a common main buffer channel 70 in fluid communication with a buffer reservoir 80. A preferable embodiment of the invention provides "split-injection" of a volume residing in the sample channel 40 defined by the length between the buffer channels 80 and 60 and the cross sectional area of the sample channel. By applying an equal or balanced (electrokinetic) force, the buffer solution within both spaced apart or split buffer channels 80 and 60 inject the sample volume or plug defined there between into the separation channel 30. The transport of an electrolyte buffer and sample is preferably accomplished by means of electric fields, which are created by switching electric potentials between electrodes of a respective wells for the sample and between electrodes associated with buffer channels and separation channel for the buffer as will be described in further detail below. (See FIG. 8)

The base portion or substrate of the microfluidic chip shown in FIG. 1 can be manufactured from glass, monocrystaline silicon or other materials known from semiconductor manufacture, or of a suitable polymer material such as poly or cyclo-olefins, polycarbonate or PMMA (polymethylmethacrylate). The chip may comprise a channel and reservoir or well system which is etched, micro-machined or otherwise established in its surface. Preferably techniques known from semiconductor manufacture can be applied for creating the channel system in the surface of the chip. The chip can be formed with through holes which communicate with the channel system and are adapted to accommodate and hold the ends of capillary tubes. The chip may be also provided with various ports (not shown) for light waveguides that can be part of an optical detection system, such as a fluorescence detection system, or an absorption detection system, or a system for the detection of changes of the refractive index of a sample flowing through the channel system. The ports can be distributed anywhere along the illustrated channel systems herein thus allowing measurements at different locations along the channel system. It shall be understood that these principles of the invention are not limited to microfluidic chips disclosed herein or for mass spectrometry applications only.

Figure 2A:
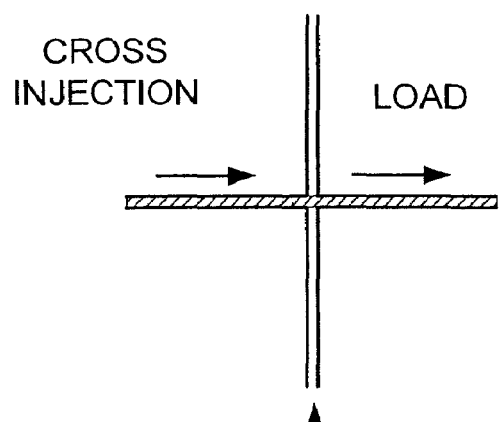
FIGS. 2A-B illustrate a sample plug formed at an intersection of channels according to a cross injection approach.
Figure 2B:
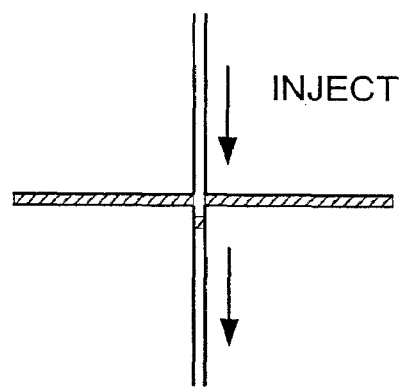

FIGS. 2A-B illustrate commonly applied procedures used to define or form a sample plug at an intersection on a microfluidic chip. By application of appropriately oriented electrical fields, a sample can be formed during a process that can be divided generally into two phases (a)-(b). During phase (a), the sample is loaded in a relatively horizontal (as shown) sample channel, from left to right, while an electrical field is applied in both segments of a relatively perpendicular separation channel from both directions towards the intersection as shown in FIG. 2A. This may be referred to as a pinched injection, and the operation of confining the sample at an intersection by applying such fields is commonly known as "pinching." The loading step can continue as long as needed for all sample components of interest to reach the intersection. Then, in phase (b), the appropriate electrical fields can be switched on to begin moving the sample plug into the separation channel and to start the separation process. Meanwhile, at the same time, another set of electrical fields can be applied in the two branches of the sample channel to begin movement of the components present away from the intersection as shown in FIG. 2B. This application of fields in the sample channel branches is commonly known as "pull-back," and it is often needed to separate the sample plug away from the rest of the excess sample being pulled back into branches of the sample channel. The absence of pull-back would likely lead to a continuous leakage of sample from the sample channels into the separation channel, which would in turn cause poor separations.

In order to elucidate the trade-offs involved in optimizing microfluidic separations, it is useful to analyze the separation performance in capillary electrophoresis. The separation quality can be determined by the magnitude of the dispersion present in a given component of a separation when it arrives at a detector. This can be expressed as:

$$\sigma^2 = \frac{w^2}{12} + 2Dt$$

where $\sigma$ is the spatial variance of the given component at the detector, w is the length of the injection plug, D is the diffusion coefficient of the molecules of the component, and t the separation time. Given that a separation time is provided by a separation length divided by relative velocity, this can also be written as:

$$\sigma^2 = \frac{w^2}{12} + \frac{2DL}{\mu E}$$

where L is the separation length, $\mu$ is the mobility, and E the electric field. This equation assumes that all other sources of dispersion, such as the size of the detector, thermal effects, wall adsorption, etc., are negligible. The quality of a separation is often characterized by N, the number of theoretical plates, which is given by:

$$N = \frac{L^2}{\sigma^2} = \frac{L^2}{\left(\frac{w^2}{12} + \frac{2DL}{\mu E}\right)}$$

More usefully, the resolution between two components in a separation is proportional to $\sqrt{N}/4$, which can be written as:

$$\frac{\sqrt{N}}{4} = \frac{L}{4\sqrt{\frac{w^2}{12} + \frac{2DL}{\mu E}}}$$

This equation shows how resolution increases as the separation length increases. Initially, when the injection plug length term dominates, the separation resolution increases linearly with separation length. In this operating region, microfluidic devices are capable of producing very rapid and high-resolution separations by their ability to control w. However, as L increases, at some point the diffusion term will start to dominate, and the resolution will increase more slowly, namely as $\sqrt{L}$. In many cases, where high resolution is needed, L will need to be increased sufficiently to reach the point where the diffusion term dominates.

Another way to look at this last equation is to analyze how separation resolution is improved as the injection plug size is reduced. For relatively large plug sizes, the improvement will be linear, up to the point where the diffusion term takes over. At that point, there is no further improvement in resolution, but the signal amplitude continues to decrease in proportion to sample plug size. In most applications, sensitivity is as important a requirement as resolution, therefore it is important to ensure that the injection plug size is large enough to optimize both sensitivity and resolution. This can be done by ensuring that the dispersion coming from the injection plug size is similar in magnitude to the dispersion due to diffusion during the separation.

Figure 3A:
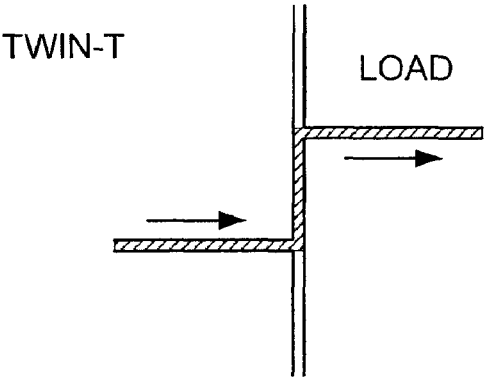
FIGS. 3A-B illustrate a sample injection according to a twin-T design.
Figure 3B:
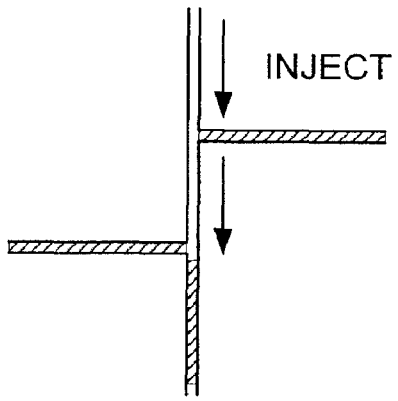

In most cases, this requirement may lead to the need for sample plugs larger than those obtained by a pinched injection at a simple intersection. Typically, such a pinched injection produces plug lengths of about 2 or 3 times the width of the channel. Several researchers have described a method of increasing the sample plug size by using an offset channel intersection, as shown in FIGS. 3A-B, sometimes referred to as a twin-T intersection. This configuration allows the injection plug size to be adjusted to desired values by changing the offset distance between the two T intersections. This has proven to be a commonly used method and the optimal sample plug size is usually considerably larger than the channel width.

However, there are some significant limitations and disadvantages associated with using the twin-T design and method of increasing a sample plug length. For example, when a twin-T design is used together with a pinched sample injection, as described above, the pinching field will cause some dilution of the material in the sample plug. As shown in FIG. 3A, the pinching current from a relatively bottom region of the separation channel will spill over into the twin-T area, where it will often dilute the sample. Thus, the twin-T structure often does not provide a completely geometric definition of the sample plug size.

Another disadvantage of the twin-T configuration is that each intersection is not symmetrical from the perspective of the side channels. To create a well-defined sample plug, during the separation phase, electrical fields in the side channel are preferably applied to remove the sample from the intersection, as described above. However, in a twin-T design, the pull-back for the two side sample channels are applied at a different time since the plug passes by these intersections at a different time. If a pull-back is applied too early, a portion of the sample plug will be unintentionally removed, and thus defeat a basic underlying purpose and function of the twin-T intersection. If pull-back is applied too late, the sample plug will have a tail portion which typically leads to poor separations. A relevant example shown in FIG. 3B depicts the initial phase of a separation during a selected time frame or window where pull-back is applied from one side of a separation channel only. The time needed for the sample plug to travel past the intersections in the twin-T depends on various factors such as the electric fields used, and also on the mobility of all the components of the sample being separated. Accordingly, this means that for each assay being performed, the optimal time offset selected for the pull-back between the two channels will be likely different each time. Moreover, this optimization in each instance can be difficult to achieve, and would not be considered particularly robust since the optimal offset time can fluctuate as a function of many parameters, including the sample composition and its conductivity. It is also not possible or feasible to attempt optimization of the time offset simultaneously for multiple components with different mobilities. The lack of symmetry with respect to the twin-T design and its associated problems with timing offset during pull-back present severe drawbacks that are avoided in accordance with the principles of the invention.

The invention provides microfluidic devices and methods for controlling sample introduction when employing microcolumn or microchannel separation techniques such as capillary electrophoresis (CE) as shown in FIG. 1. An electrolyte buffer and a concentrated sample are transported through a system of capillary channels of various designs and geometries. The sample is injected as a sample plug within a device which comprises channels for the electrolyte buffer and a sample loading channel and a waste channel, which can be viewed as two distinct channels in practice or different portions of a same sample channel. The channels for directing the electrolyte buffer, the sample loading channel and the waste channel for the sample may be formed to intersect each other.

In some embodiments, the separation channel is positioned relatively on-center with respect to the position of the buffer channels that are equally spaced apart from the separation channel. A portion of a sample plug may be injected or discharged into the separation channel from a portion of the sample loading channel and waste channel, which may be substantially aligned relative another as shown in FIG. 1. The section of the sample channel measured by a distance between the outermost boundaries of the two buffer channels where they intersect the sample channel can be chosen to geometrically define a sample volume. The buffer channels and the separation channel can be each inclined or perpendicular to the sample channel. The injection of the sample plug into the sample channel can be accomplished electrokinetically by applying an electric field across the sample well and the waste channel for a time at least long enough that the sample component having the lowest electrophoretic mobility is contained within the geometrically defined volume. It shall be understood that the movement of the sample can also be accomplished by other driving forces such as pressure which are apparent to those of ordinary skill in the field.

In a further or subsequent step, following the introduction of sample into the defined portion of the sample channel between the buffer channels, the electrolyte buffer may be (electrokinetically) advanced into the buffer channels symmetrically for a preselected period of time so that the well defined sample plug is injected into the separation channel. The amount of time selected may be equal to at least the migration time of a slowest component within the sample plug from the intersection point between the buffer channel and the sample channel. In addition, a portion of the sample can be pushed back into the respective sample and waste channels and substantially prevented from uncontrollably diffusing into the electrolyte buffer which is transported in the sample channel. These methods provided in accordance with this aspect of the invention controls leakage of sample composition into the electrolyte buffer (see FIGS. 4A-C).

In order to ensure that the composition of the sample plug actually reflects the actual sample composition, the electric field across the sample and waste channels is preferably maintained for at least for a time period long enough that the geometrically defined sample volume is filled and contains the component of the sample which has the lowest electrophoretic mobility. This minimum time period $t_{min}$ is given by the equation $t_{min} = d/\mu_i . E$. In this equation d stands for the distance between the outermost boundaries of the two buffer channels where they intersect the sample channel; $\mu_i$ is the total mobility of the slowest component i of the sample; E is the field strength across the loading and waste channels, which results from the difference in potentials.

The sample can be introduced from the sample well to the sample waste well by application of appropriately oriented electrical fields ranging from at least 0.1-1000 V/cm or greater. The sample channel portion that defines the sample plug is the distance between the outermost boundaries of the two buffer channels where they intersect the sample channel. The buffer channels may be equidistant from the separation channel or may be symmetrically placed on either side of the separation channel. Thus, the sample channel portion of the sampling device defines the volume of the electrokinetically injected sample plug. In other words, the volume of the sample plug is geometrically defined by the spaced apart outermost boundaries of the two buffer channels where they intersect the sample channel. By this measure the composition of the injected sample plug can reflect the actual sample composition.

When an electrophoretic analysis of a sample is to be carried out, an amount of electrolyte buffer is transported from the buffer channel to the separation channel. After the channel system of the chemical analysis system has been filled with the electrolyte buffer, the directing sample into the channel can be initiated (or alternatively, the buffer solution need not precede introduction of the sample). An electric field can be established between the sample well and the waste well such that sample is electrokinetically transported through the sample channel towards the waste channel and eventually into the waste well. It is understood that during the time period in which the sample is loaded, the electric field between the buffer channel and the separation channel is switched off, or that the potentials are chosen such that the sample only is transported along the path described above. After the selected time period for applying the potential has elapsed to ensure that the sample volume between the sample well and the waste well is filled with the sample, the electric field between the sample well and the waste well is switched off. At the same time an electric field between the buffer channel and the separation channel can be activated again such that at least a portion of the sample contained within the sample channel is transported into the separation channel. While the sample travels along the separation channel, the sample volume can be separated electrophoretically under the influence the applied electric field.

The problem of leakage or diffusion of sample components into the electrolyte buffer while it is transported past the sample channel, even though no electric field is applied between the sample well and the waste well, is solved by allowing the electrolyte buffer to advance into the sample loading channel and into the waste channel for a time period, which amounts to at least part of the migration time to of the slowest component (i) within the sample plug from the sample chamber to the respective detector. Thus, the sample is pushed back into the sample loading and waste channels and substantially prevented from uncontrollably diffusing into the electrolyte buffer.

The migration time $t_i$ of the slowest component i of the sample is defined as the quotient between the separation length L and the product of the total mobility $\mu_t$ of the slowest component i of the sample and the electric field strength E' acting on it along its path L, and is given by the equation $T_i = L/(\mu_t . E')$. In this equation the separation length L is the distance the sample component i travels from the first intersection between the electrolyte buffer channel and the sample channel, and the respective activated detector, and the total mobility $\mu_t$ of the component is the sum of the electrophoretic mobility $\mu_{i,ep}$ of the component and the overall electro-osmotic mobility $\mu_{eo}$ of the sample. The time period during which the detection is accomplished is very short in comparison to the migration time of the slowest component of the sample and thus is negligible.

Various approaches to produce electrokinetic advancement of a buffer solution and a sample within a microfluidic device as described above are depicted in FIGS. 4-13. Methods and microfluidic devices provided herein include electrokinetic movement of the buffer and defined sample plug through the channels throughout herein. It should be noted however that the movement of sample and buffer can also be accomplished by other driving forces such as pressure driven alternatives. It should be further noted that the microfluidic devices illustrated herein may also include the apparatus formed with channels which are rotated by 90 degrees such that the buffer channel are shown relatively horizontal and the sample well relatively vertical.

Figure 4A:
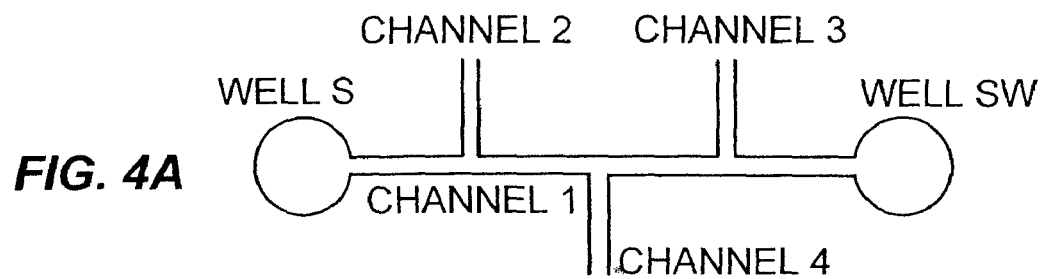
FIGS. 4A-C illustrate a sample plug between arms of a multiple injection channels.
Figure 4B:
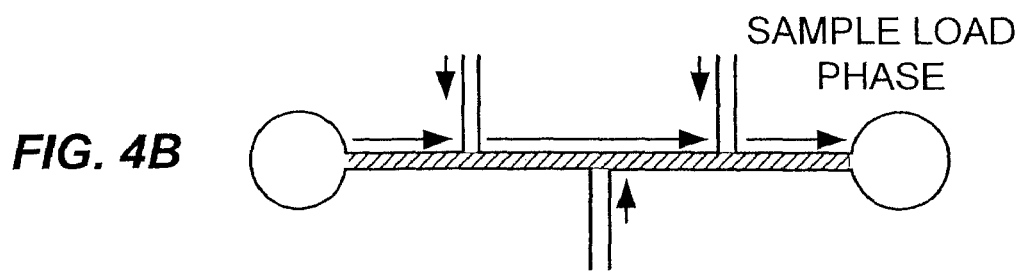
Figure 4C:
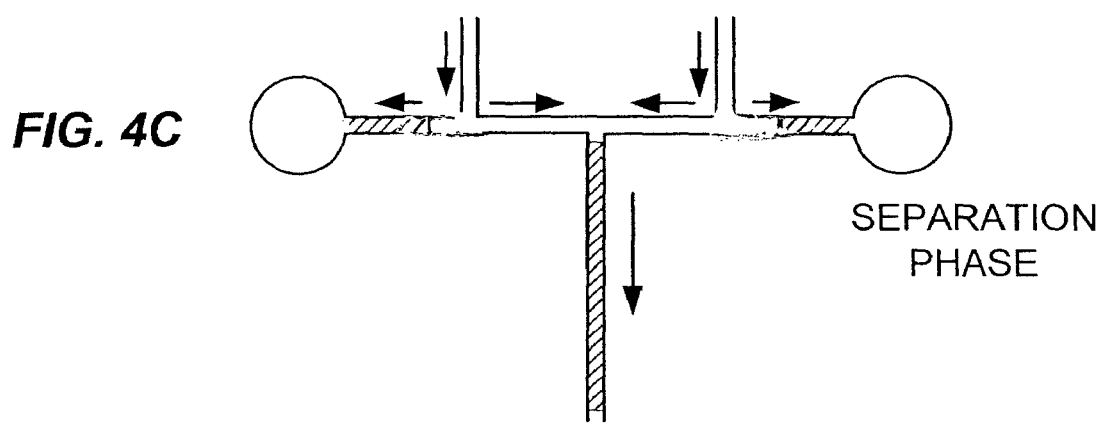

An aspect of the invention provides methods to achieve sample volumes relatively larger or better defined than those formed by following conventional twin-T methods. FIGS. 4A-C illustrate a sample plug between arms of a multiple injection channels which are buffer channels. The two injection channels can intersect the sample channel at some distance with a separation channel in between the injection channels. Each injection channel may then be used to define one end of a sample plug along the sample loading channel. Once the sample is loaded along the entire or predefined length of the sample channel, an electric field (or with a pressure difference) can be applied to define a sample plug. When applied, the electric field can move the sample away from each of the injection channels. The sample portion that lies between the injection channels can be directed into the separation channel. The sample that is not in this area can then be directed further away from the separation channel, which can minimize leakage. By separating the two ends of the sample plug simultaneously in accordance with the split injection techniques and systems herein, the size of the plug may be chosen independent of the mobility of the sample components. The separation may also involve only two phases, namely, sample loading followed by separation with pull-back. An intermediate phase of separation with less or no pull-back may not be needed. Furthermore, tailing may be avoided by keeping the dimensions of the channel or chamber small, preferably around the intersections. These and other benefits provided in accordance with the invention are described below in further detail.

FIG. 4A illustrates a topology of a sample injection device where a well S contains a sample and channels 2 and 3 contain a separation buffer. FIG. 4B shows a sample load phase where sample is transported along a sample loading channel from the sample well S towards a sample waste well SW. The arrows within the figures indicate a direction of electrokinetically driven sample movement, and the direction of the pinching in the side channels to keep the sample confined to sample channel. It is desirable to keep the pinching currents as small as possible, to minimize the dilution of the sample in the sample loading channel. The arrows in the figure can also illustrate the direction in which sample is transported, which may not be the same as the direction of the electric current. Transport may go in the direction of the electrical field, multiplied by the net sum (including sign) of the electrophoretic mobility and the electroosmotic mobility of the sample. FIGS. 4C illustrates a separation phase with pull-back. The two halves of the sample plug in the sample channel relative to the separation channel may be injected into a separation channel 4 while pull-back is applied on outer portions of channel 1. The arrows in this figure indicate a direction of electrokinetically driven sample movement and the direction of the pull-back in the sample loading channels along with the leakage of the sample into the separation channel. FIGS. 4B-C show the direction of the currents during this phase. The two currents in the separation buffer channels may be identical to avoid time offset in the merge. Without limiting the scope of the invention, the movement of the sample can also be accomplished by other driving forces such as pressure.

Figure 5A:
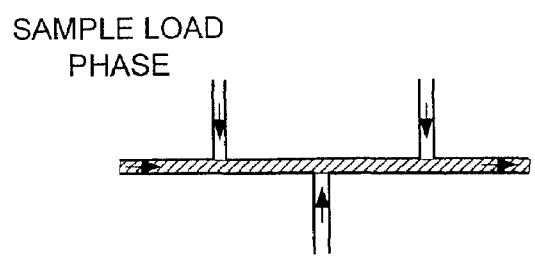
FIGS. 5A-C illustrate a sample plug formed between arms of a multiple injection channels.
Figure 5B:
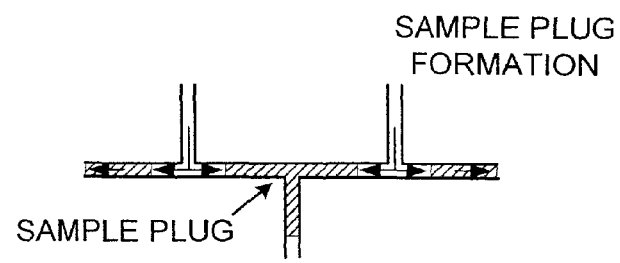
Figure 5C:
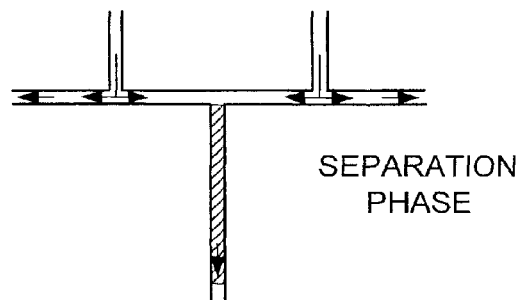

FIGS. 5A-C illustrate another embodiment of the invention that forms a sample plug between a multiple injection channels. The arrows indicate a direction of pressure or electrokinetically driven sample movement. FIG. 5A shows a sample load phase where a sample is transported along a sample loading channel in addition to application of a pinching current to keep the sample confined to sample channel. FIG. 5B illustrates the split injection of the sample volume formed between the injection channels into a separation channel or other channel formed on a microfluidic device that delivers the well defined plug for further analysis, separation or other selected procedure. FIG. 5C illustrates the direction of the buffer or other solution from the injection channels into the sample channel while directing the sample plug into the separation channel.

Figure 6A:
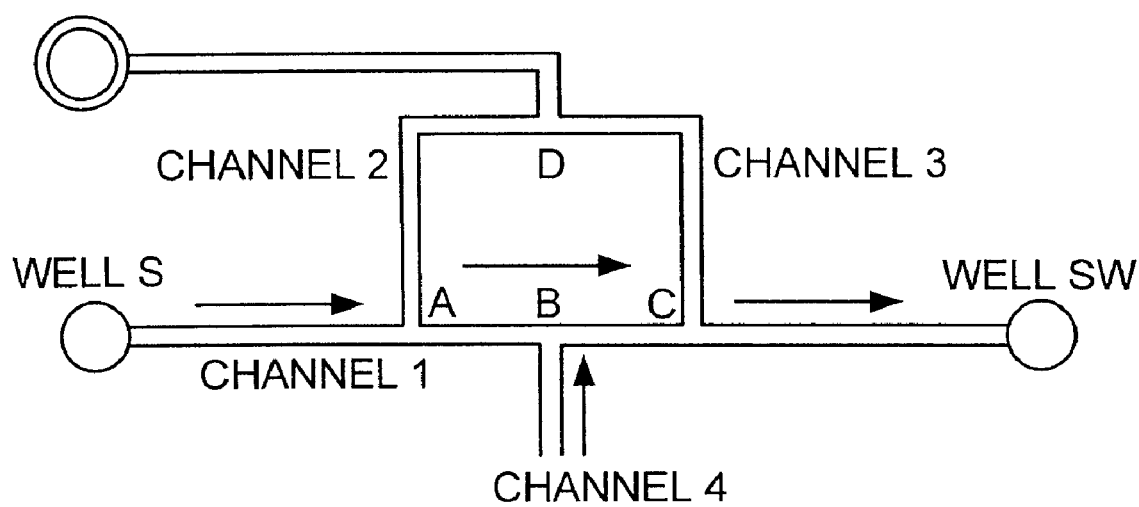
FIG. 6A illustrates a sample plug between arms of split injection channels where the injection channels are connected to a single well.

Another aspect of the invention herein provides methods for defining a sample plug between the arms of a split injection channel (main buffer channel). FIGS. 6A illustrates a sample plug between arms of split injection channels 2 and 3. The two injection channels 2 and 3 can be connected to a single well, while maintain the shape and dimensions of the two injection channels identical and symmetrical. The directions of the arrows indicate the desired direction of sample transport during the load phase from the sample well S to sample waste well SW. The left-to-right symmetry of the device can ensure that the two currents in the split injection channels are equal provided that they are filled with a solution with constant conductivity and electroosmotic mobility. Another advantage of this configuration is that only a single well may be needed for the separation buffer as minimizing the number of wells is typically desirable to save valuable space. In an alternate embodiment shown in FIG. 6C, the split injection channels can be fluidly connected and attached to separate wells.

During a load phase as shown in FIG. 6A, the merged channels 2 and 3 may cause an issue with respect to the pinching needed to confine the sample to the loading channel only. The current flow (I) between selected channel intersection points or nodes in are illustrated below in FIG. 6B (A, B, C and D). If the current $I_{AD}$ goes in the direction opposite of that depicted in FIG. 6A, then the sample may bleed into the channel between nodes A and D, and further into channel 3. This may make the sample injection unequal, and uncontrolled, since the extent to which sample may leak into channels 2 and 3 depends on the loading time, and the mobility of the sample components.

Figure 6B:
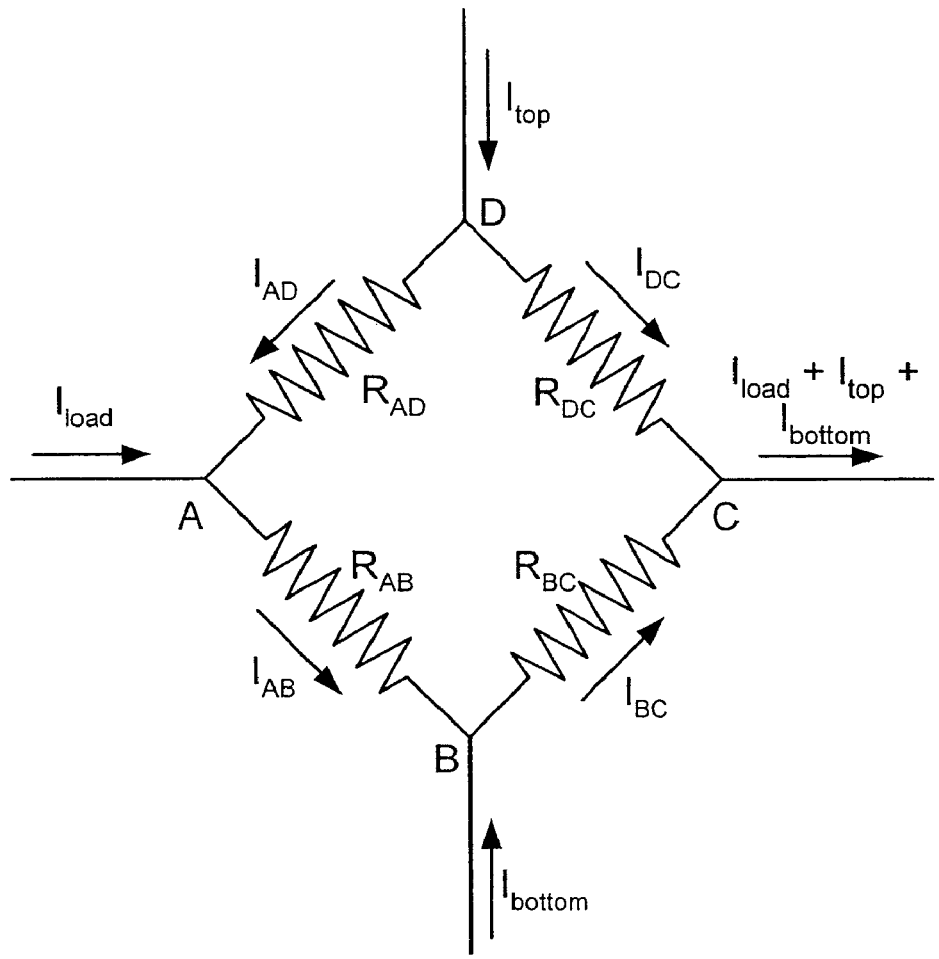
FIG. 6B illustrates an electrical analog of a chip geometry, including the nodes A through D, and conceptual resistors between them.
Figure 6C:
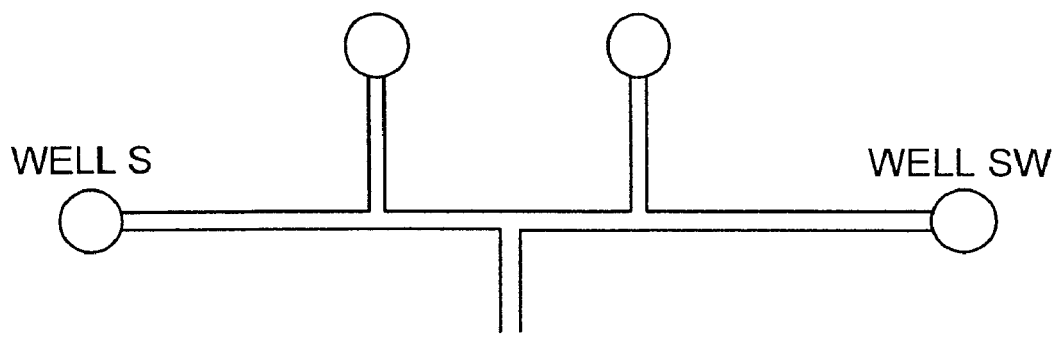
FIG. 6C illustrates split injection channels attached to separate wells.

The current $I_{AD}$ can be calculated in terms of the known resistances and the currents at the wells $I_L$ (the loading current), $I_T$ (the top pinching current), and $I_B$ (the bottom pinching current). FIG. 6B shows an electrical analog of the microfluidic chip geometry, including the nodes A through D, and resistors between them. In FIG. 6A, following expression for the current $I_{AD}$ in the branch AD may be:

$$I_{AD} = [I_T R_{AD} - (2I_L + I_B) R_{AD}]/[2(R_{AB} + R_{AD})]$$

If the pinching ratios are defined as $p_T = I_T/I_L$ and $p_B = I_B/I_L$, the condition that may ensure that the current $I_{AD}$ stays positive can be written as:

$$p_T(R_{AD}/R_{AB}) > 2 + p_B$$

This may mean that it may be necessary to design the resistance ratio and the top pinching ratio to be large enough, to meet the condition as stated above.

Figure 7A:
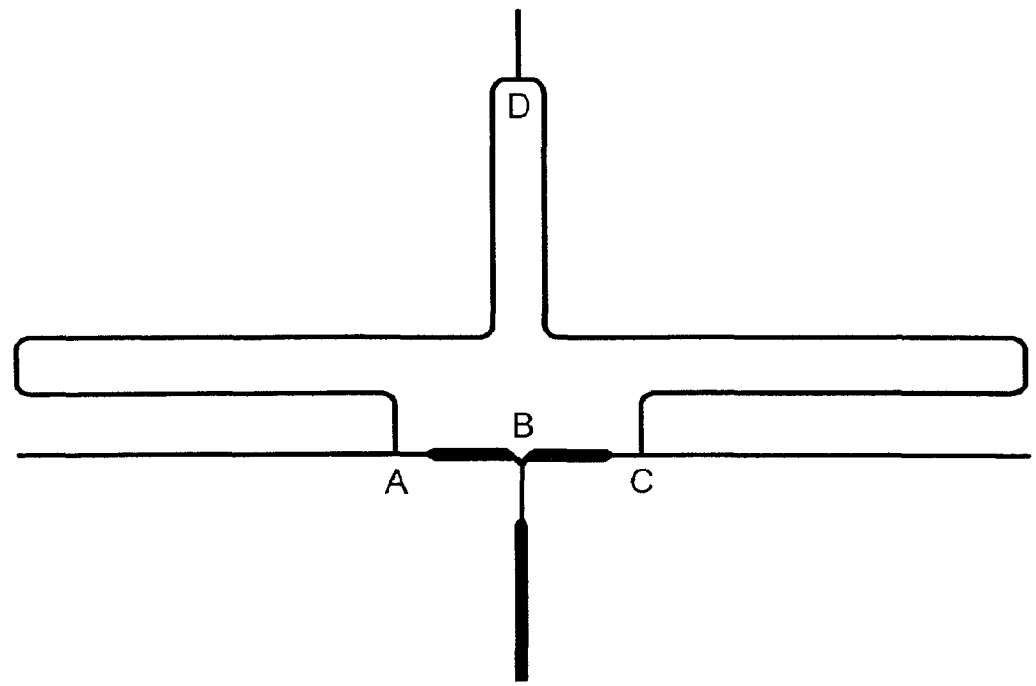
FIG. 7A illustrates a geometry with wider channels between A and B and between B and C, combined with long and narrow channels between A and D and between D and C. The channels are narrower in the vicinity of intersections A, B, and C.
Figure 7B:
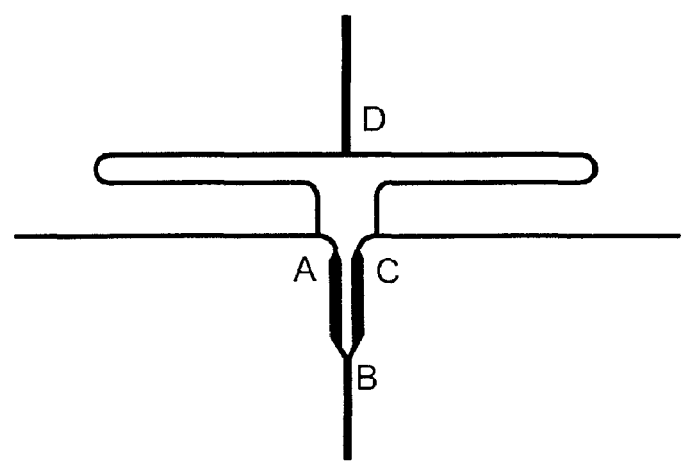
FIG. 7B illustrates the section between A and C folded to make the structure more compact.

By increasing the resistance ratio $R_{AD}/R_{AB}$, while keeping the volume defined along the loading channel the same, it may be possible to make the sample channel between nodes A and C wider and shorter. It may also be desirable to reduce tailing and to improve speed of a creation of the sample plug at nodes A and C. It can be achieved by keeping the channels as narrow as possible around nodes A, B, and C. This leads to structures such as those shown in FIGS. 7A-B. FIG. 7A illustrates a geometry with relatively wider channels between A and B, and between B and C, combined with long and narrow channels between A and D and between D and C. In addition, the channels are narrower in the vicinity of intersections A, B, and C. A further option is to fold the section between A and C to make the structure more compact as illustrated in FIG. 7B. The choice between the structures of FIGS. 7A and 7B can be made based on whether compactness in the horizontal or vertical dimension is more desirable. The type of structure shown in FIG. 7A may be preferred, if more room is needed horizontally than vertically. All the variations shown in FIGS. 7A and 7B are substantially equivalent in terms of their topology and are alternate embodiments provided in accordance with this aspect of the invention. As with other embodiments described herein, all channels (alternately referred to as microchannels throughout herein) can vary in dimensions (both depth and width), and can contain various turns and bends, without affecting the operation and topology of the invention.

Figure 8:
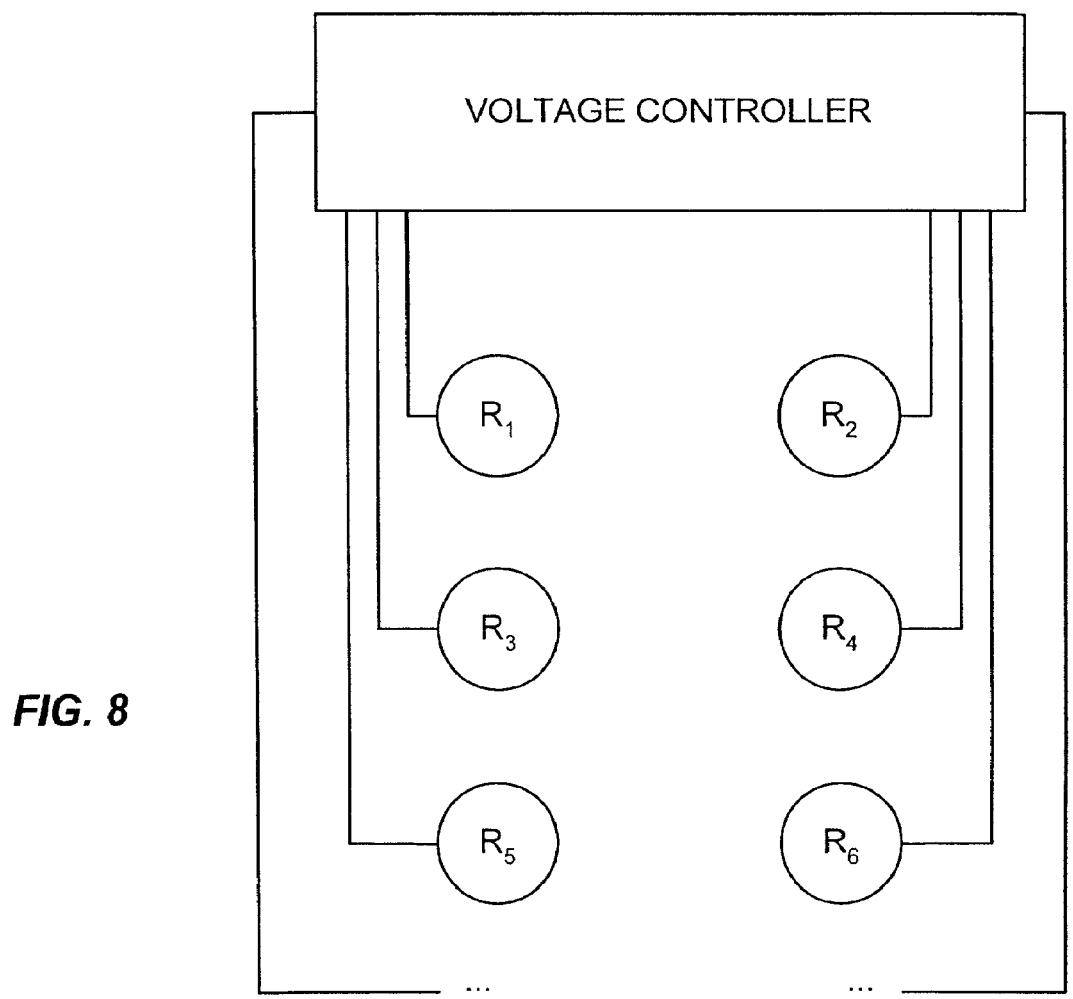
FIG. 8 illustrates an example of a microchip laboratory system including six reservoirs $R_1$, $R_2$, $R_3$, $R_4$, $R_5$, and $R_6$ connected to each other by a system of channels.

FIG. 8 is an example of a voltage control system for a microchip laboratory system. The laboratory system includes six wells or reservoirs R1, R2, R3, R4, R5, and R6 connected to a microchannel network formed upon the microchip (any number of reservoirs and corresponding channels can be selected optionally). Each well may be in fluid communication with a corresponding channel of the channel system. The materials stored in the wells preferably are transported electrokinetically through the channel system in order to implement the desired analysis or synthesis. To provide such electrokinetic transport, the laboratory system may include a voltage controller capable of applying selectable voltage levels, including ground, via electrodes positioned at each reservoir. Such a voltage controller can be implemented using multiple voltage dividers and multiple relays to obtain the selectable voltage levels. The voltage controller may be connected to an electrode positioned in each of the six wells by voltage lines in order to apply the desired voltages to the materials in the wells. The voltage controller may also preferably include sensor channels in order to sense the voltages present at those intersections. It shall be understood that electrokinetic movement can be directed on microfluidic devices herein in accordance with this aspect of the invention.

Figure 9:
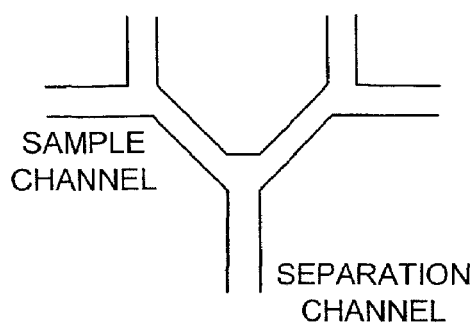
FIG. 9 illustrates a different geometry for the area between the injection channels that defines the sample plug.

FIG. 9 illustrates a different geometry for the area between the injection channels that defines the sample plug. In this embodiment, the sample channel portion between the injection channels forms a general V- or U-shaped configuration. Rather than positioning a sample load channel substantially aligned with a sample drain channel, a channel kink or detour may be formed which may in turn provide a relatively greater sample volume. The total linear distance or sample channel length formed between the injection channels is greater than alternate embodiments where the sample channel is strictly linear in this region.

Figure 10:
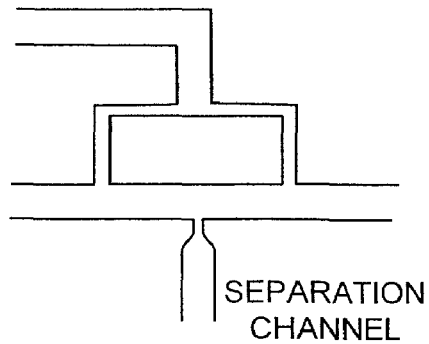
FIG. 10 illustrates a design feature where a channel or channel portion leading up to the sample channel is narrower and/or shallower.

Another aspect of the invention provides a design feature that could be applied to provide connections to a sample channel section that are relatively narrower and/or shallower than the other channel portions leading up to the section as shown in FIG. 10 (or FIG. 7A). The injection channel may be formed with a smaller cross-section relative to the sample channel, and at the same time a separation channel can be formed with a narrowed region that connects to the sample channel. These alternate modifications may facilitate both the pinching process in the first step, and the pull-back in the second step of a separation, in the case that there are also pressure sources present. These pressure sources can be intentionally used (in the sample loading step, for instance), or may be unintended due to other considerations such as the surface tension forces at the wells at the end of the channels, or the negative pressure caused by an electrospray ionization device at the end of a channel. In microfluidic devices used under real or actual operating conditions, external pressure sources tend to be always present to some extent. A portion of these channels with reduced cross-sectional area can both amplify the effect of the electrokinetic forces, since the electric field is higher, and reduce the effect of external pressures since the hydrodynamic resistance is usually higher. Accordingly, the result is to create a zone where the pinching and the sample pull-back will occur with greater ease and precision.

Some of the sampling devices according to the invention have been described with reference to exemplary embodiments utilized as micro-analysis chips. The buffer and separation channels may be inclined to the longitudinal extension of the sample channel at an angle that may amount to from about 5 degrees to about 175 degrees; however, preferably they are arranged about perpendicular with respect to the sample channel. Without limiting the scope of the invention, the chip may be present at a rotation of 90 degrees in such a way that buffer channel is horizontal and the sample channel is vertical. The distance d which is a section of the sample channel which is the distance between the outermost boundaries of the two buffer channels where they intersect the sample channel, may amounts to from about 1 μm to about 3 cm.

The sampling devices provided in accordance with the invention can also include an arrangement of capillary tunnels, which can be part of a electrophoretic chemical analysis system made of capillary tunnels. In some embodiments, however, the sampling device can be integrated into a system of capillary channels which are established in a small planar sheet of glass, semiconductor material, or a suitable polymer. Advantageously the channel system including the buffer and separation channels may be molded or etched or micromachined or cast (in case of a polymer base part), or otherwise established in the planar substrate. Most suitable for its manufacture are techniques which are well established in semiconductor production or in the manufacture of micromechanical elements. It shall be understood that as with other designs and concepts presented herein, this aspect of the invention can be combined in many possible variations known to those of ordinary skill in the field.

Figure 11A:
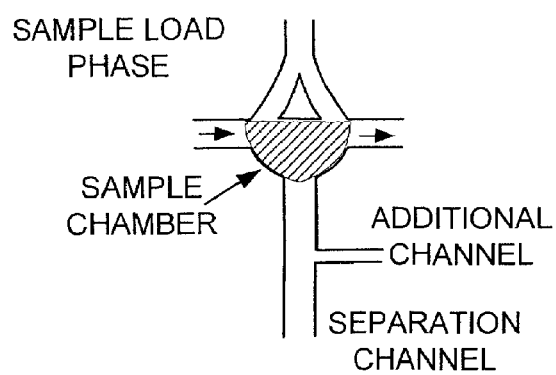
FIGS. 11A-C illustrate a curved shaped geometry of the area between the injection channels that define the sample channel. Additional channel is added downstream for separation.
Figure 11B:
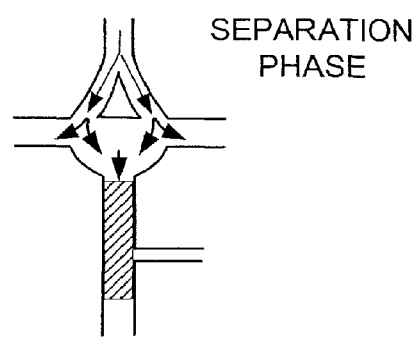
Figure 11C:
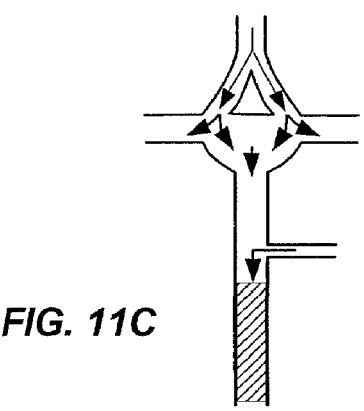

FIGS. 11A-C illustrate another aspect of the invention showing an alternate geometry for the area between the injection channels that define a sample chamber (cross-hatched section). The volume of the sample chamber can be increased by producing a larger cavity of curved (semi-circular) shape, or otherwise modified for a selected volume. An additional channel connected to an exit channel may be added downstream for separation or other procedure. The sample chamber can be formed with a substantially diamond shape or a circular or curved shape positioned at a location where channels connecting to the chamber would otherwise intersect. It should be observed that the size of the sample chamber structure does not have to be very large in order to provide the same comparable volume that is defined by a channel section between a twin-T intersection. The microstructures for defining samples provided herein are not restricted or confined by the limitations of a channel structure. For instance, a diamond shape chamber measuring 330 microns along each side will have the same area as a 2 mm long segment of a 50 micron wide channel. The precise shape of the chamber may not be relatively important; for instance the walls in some variations of the inventions may be curved as shown in FIG. 11A to increase the chamber volume. It shall be understood that concepts of the invention can be applied to a variety of microfluidic chambers including but not limited to those described in U.S. patent application Ser. No. 11/278,132 filed on Mar. 20, 2006, which is incorporated by reference in its entirety herein.

The microstructures for defining samples provided herein may also provide microchambers formed with varying depths to provide increased sample volumes. The selected volume of a sample chamber can be increased or otherwise modified by increasing or modifying the depth of the microstructure. The relative depth of the sample chamber may be greater or different relative to the depth selected in fabricating the channels. For example, as shown in FIG. 11A, by way of example only, in the cross-hatched section, the channels can be 30 microns deep. It is quite feasible to also fabricate a chamber that is 100 to 200 microns deep. That would allow considerably greater sample volumes to be created yet occupy the same amount of space or footprint size along the lateral dimensions (two dimensions) of the microfluidic device.

It should be noted that when implementing this embodiment of the invention with pinching fields, there can be some dilution of the material in the chamber. However, compared to a twin-T configuration, the fraction of the chamber volume lost is relatively much smaller because the chamber dimensions are larger than a channel width. This may allow the use of lower pinching current. The amount of sample injected can be therefore expected to be more closely equal to the intended geometrically defined volume.

Figure 12A:
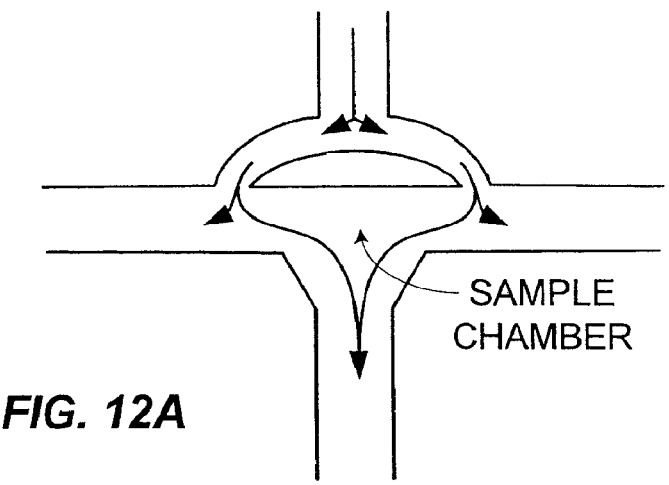
FIGS. 12A illustrates a curved shaped geometry of a sample chamber formed at a location where channels connecting to the chamber would otherwise intersect.
Figure 12B:
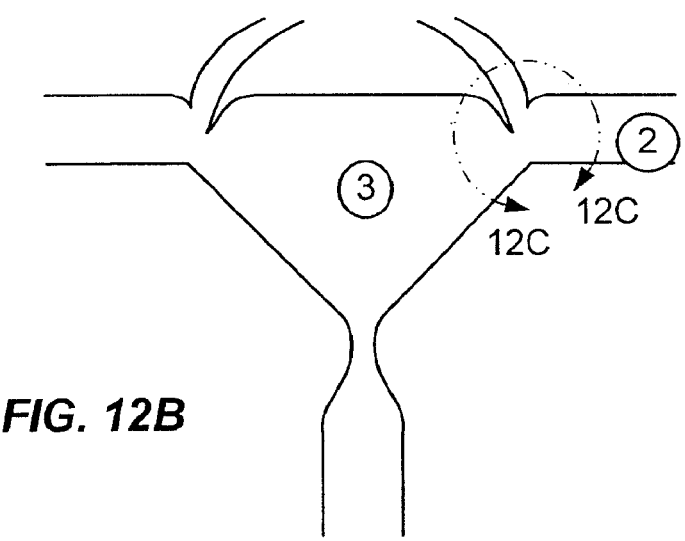
FIG. 12B illustrates a curved shaped geometry of a sample chamber with the narrowing of down stream channel.
Figure 12C:
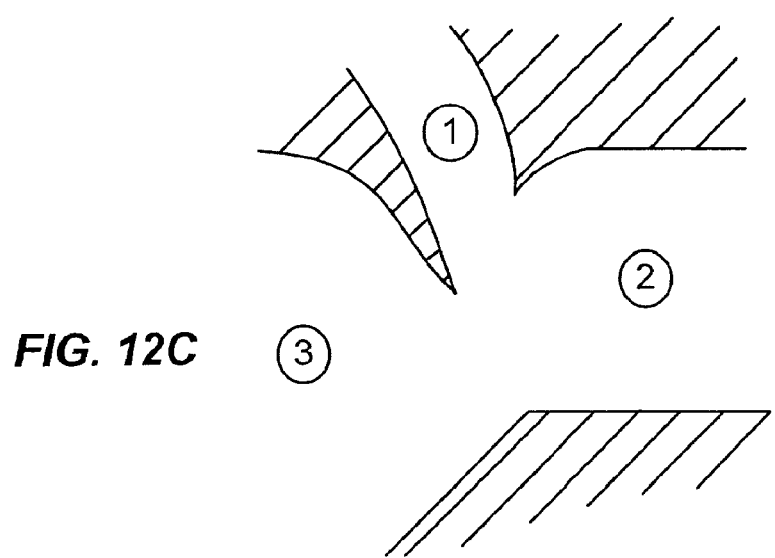
FIG. 12C illustrates an enlarged view of a portion of FIG. 12B.

FIGS. 12A-B illustrate different geometries for the area between the split injection channels that define sample chambers. The sample chambers are formed with a substantially a circular or curved shape positioned at a location where channels connecting to the chamber would otherwise intersect. Narrowing of down stream channel as shown in FIG. 12B provides filling of a triangle chamber (or generally triangular shaped sample chamber) without filling the downstream channel. FIG. 12C illustrates an enlarged view of a portion of FIG. 12B. During the sample loading step, much of the sample may be directed into a triangle chamber 3. The resistance from a sample waste channel 2 to the triangle chamber 3 may be lower than the resistance from the sample waste channel 2 to an injection channel 1. This may help confine the sample to the triangle chamber 3 with less leakage into channel 1. Similarly, the resistance from the triangle chamber 3 to the sample waste channel 2 may be lower than the resistance from the triangle chamber 3 to an injection channel 1. This may prevent the loading of the sample in the sample waste channel 2.

In order to inject the defined sample portion into the separation channel, the channel 1 may be at the highest potential followed by the channel 2 and the triangle chamber 3. The flow from channel 1 may be split between the channel 2 and the triangle chamber 3. This may lead to a bulk of the flow from the channel 1 to the channel 2 to define the sample region. The remaining flow from the channel 1 may push into the triangle chamber 3 forcing the sample out of the loading region and into the separation channel.

Figure 12D:
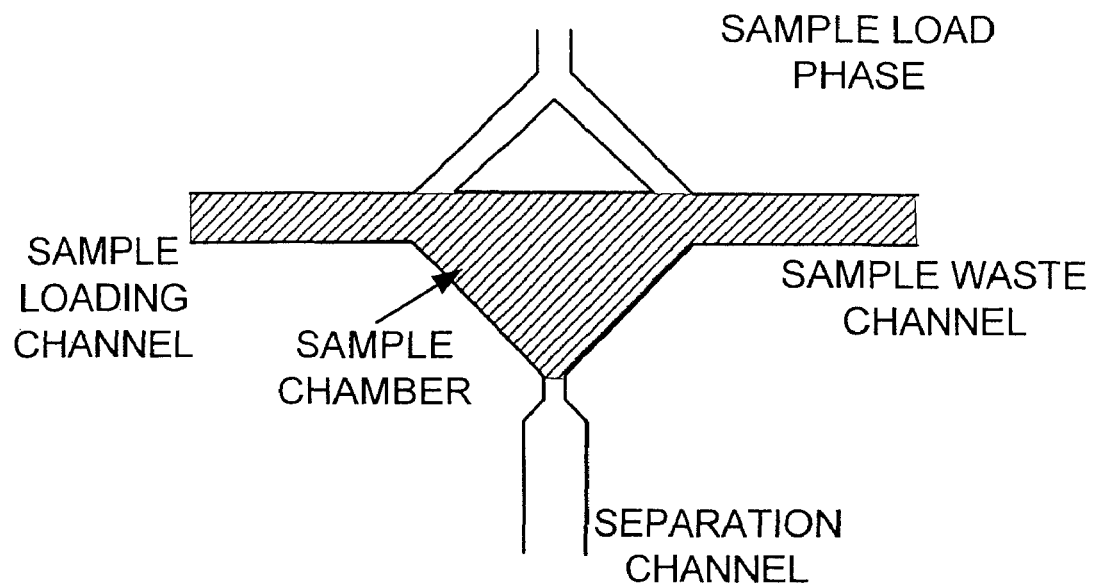
FIGS. 12D and 12E, respectively, illustrate a sample load phase and a separation phase for FIG. 12B.
Figure 12E:
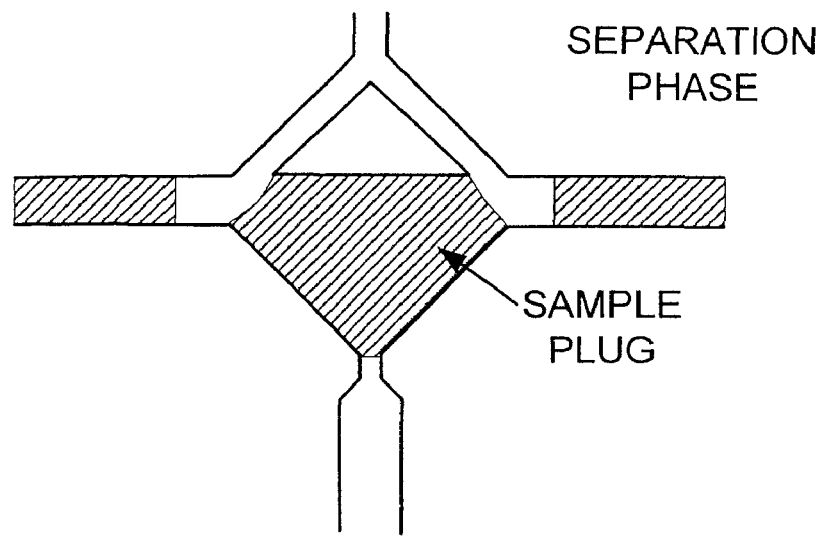

FIGS. 12D and 12E, respectively, illustrate a sample load phase and a separation phase for the sample chamber configuration illustrated in FIG. 12B. The sample is indicated by the hatched area. The direction of the pinching in the side channels can generally keep the sample confined to sample plug separating it from the sample loading and the sample waste channels. To form a well defined sample plug, leakage into the injection and separation channels during the loading step can be minimized by using a combination of electric fields and differences in hydrodynamic resistance in the sample plug regions and the regions where the injection and separation channels intersect the sample channels.

Figure 13A:
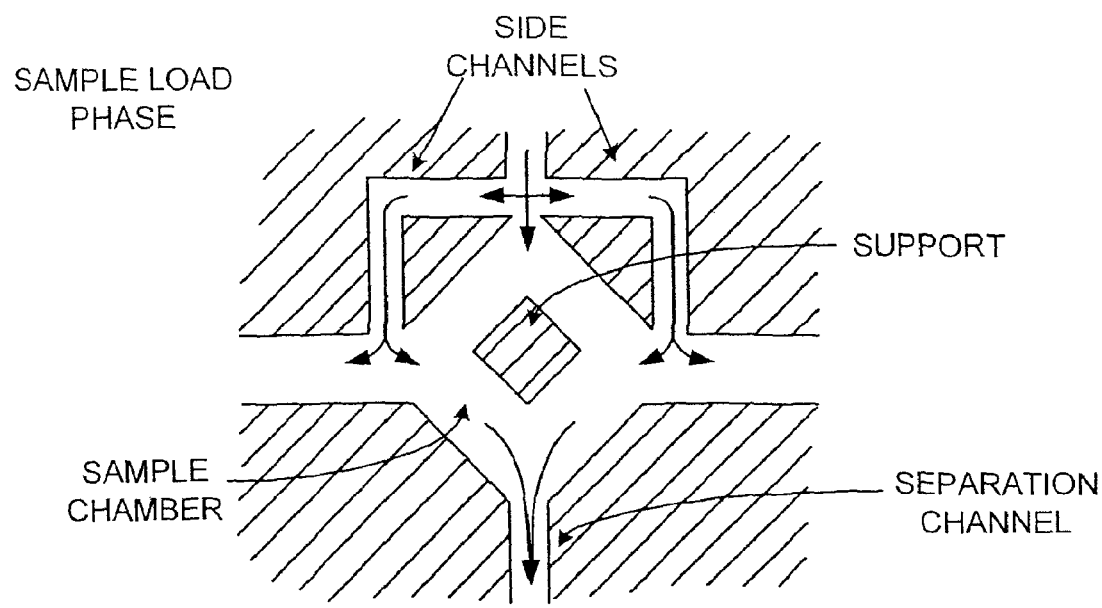
FIGS. 13A-B illustrate a design feature where a sample chamber is formed with a substantially diamond shape positioned at a location where channels connecting to the chamber would otherwise intersect. The channel upstream of the sample chamber splits and intersects the sample chamber from both the sides.
Figure 13B:
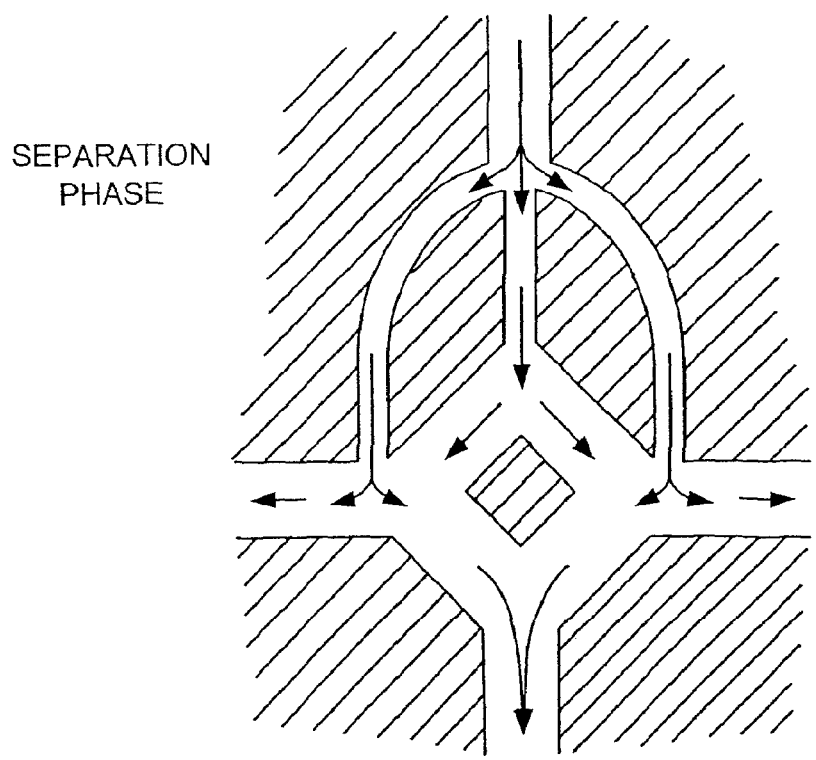

Another aspect of the invention herein provides a design feature where the sample chamber is formed with a substantially diamond shape positioned at a location where channels connecting to the chamber would otherwise intersect. The channel upstream of the sample chamber splits and intersects the sample chamber from both the sides as illustrated in FIGS. 13A-B. The two side channels may facilitate the transport of the sample to the sample chamber more effectively.

The use of a relatively large sample chambers in accordance with certain applications of the invention may entail additional modifications to microfluidic devices. For example, in some fabrication processes, a covered large open area may tend to sag in a middle region if no support is present, particularly if the device is made of polymeric materials. The illustrations of the invention herein will include a covering or cover layer that encloses an underlying substrate layer wherein selected sample chambers can be formed. With certain microstructures, it has been observed that areas up to 100 or 200 microns wide typically present no apparent problems with sagging. But beyond that range of sizes, it may be preferable to construct and provide some mechanical support for the enclosed chamber to prevent sagging of the chamber covering as shown in the example depicted in FIG. 13A-B.

Another benefit conferred by a central support structure is to ensure a sample flow with less dispersion when moving from a sample microchamber into an adjacent separation channel. The material within the middle region of the sample flow would otherwise travel relatively faster than that at the edges without such as support structure. By limiting the width of an open area within the sample microchamber, such dispersion can be thereby reduced or minimized. As shown in FIG. 13A-B, the diamond shaped chamber has a central support structure occupying a volume of the sample microchamber which avoids creating an open area that is too large. Accordingly, a central support structure for the sample microstructures herein can serve alternate purposes and may provide what may be characterized as a spacer to control and vary the desired volume with a relatively larger sample microchamber.

Another type of structure that can provide a central support to avoid or reduce sagging may utilize a multiplicity of smaller support structures. Selected support structures formed in accordance with this embodiment of the invention have an advantage of being able to provide a maximal amount of support with a minimal impact on the sample volume in the chamber.

The overall symmetry and balance of the designs provided herein effectively enables pull-back to be performed with electrical fields applied from both sides of the microchamber at the same time. It shall be understood that these and other benefits provided by the invention present symmetry when maintaining the relative left/right symmetry (as shown in the figures herein with relatively horizontal sample loading channel), but also for applications when modifying the relative up/down symmetry.

While the invention has been described with reference to the aforementioned specification, the descriptions and illustrations of the preferable embodiments herein are not meant to be construed in a limiting sense. It shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art upon reference to the present disclosure. It is therefore contemplated that the appended claims shall also cover any such modifications, variations and equivalents.

The invention claimed is:

1. A microfluidic device for sample injection which comprises
   a sample channel, which contains a sample having an original sample composition, a separation channel, and two buffer channels, which contain an electrolyte buffer,
   wherein the buffer and separation channels each intersect the sample channel, and the separation channel is positioned between the buffer channels, such that a sample volume is substantially defined by a section of the sample channel between the outermost boundaries of the two buffer channels where they intersect the sample channel.

2. The microfluidic device of claim 1 wherein the two buffer channels are connected to a single well.

3. The microfluidic device of claim 1 wherein the two buffer channels are connected to two separate wells.

4. The microfluidic device of claim 1 wherein a portion of the buffer or separation channels is defined with a reduced cross-sectional area relative to the width of a sample loading channel portion of the sample channel.

5. The microfluidic device of claim 1 wherein the sample volume is geometrically defined.

6. The microfluidic device of claim 1 wherein the sample volume can be further defined by a sample chamber with variable depth.

7. The microfluidic device of claim 6 wherein a dimension of the sample chamber is relatively greater than the width of a sample loading channel portion of the sample channel or separation channel.

8. The microfluidic device of claim 6 wherein the sample chamber is selected from one of the following: a diamond shape, a circular shape or a curve shape.

9. The microfluidic device of claim 8 wherein the sample chamber is formed with a depth different than that of the sample loading channel portion of the sample channel or separation channel.

10. The microfluidic device of claim 8 wherein a portion of the buffer or separation channels is defined with a reduced cross-sectional area relative to the width of a sample loading channel portion of the sample channel.

11. A method of introducing a sample into a microfluidic device, which microfluidic device comprising
    a sample channel connected to a sample well and a waste well at the two separate ends, where the sample well contains a sample having an original sample composition, two buffer channels, which contain an electrolyte buffer, and a separation channel,
    wherein the buffer and separation channels are each inclined with respect to the sample channel, and the separation channel is between the buffer channels,
    and wherein buffer and separation channels intersect the sample channel, such that a geometrically defined sample chamber is a sample volume defined by a section of the sample channel located between the outermost boundaries of the two buffer channels where they intersect the sample channel,
    which method comprises the step of electrokinetically loading a sample plug into the sample channel by applying an electric field across the sample well and the waste well, wherein the electric field is applied for a time period which is at least long enough that the component of the sample having the lowest electrophoretic mobility migrates into the geometrically defined sample chamber, such that the loaded sample plug reflects the original sample composition.

12. The method of claim 11 wherein the two buffer channels are connected to a single well.

13. The method of claim 11 wherein the two buffer channels are connected to two separate wells.

14. The method of claim 11 wherein a portion of the buffer or separation channels is defined with a reduced cross-sectional area relative to the width of a sample loading channel portion of the sample channel.

15. The method of claim 11 wherein the loaded sample plug is injected into the separation channel.

16. The method of claim 11 wherein the sample volume can be further defined by a variable depth of the sample chamber.

17. The method of claim 11 wherein a dimension of the sample chamber is relatively greater than the width of a sample loading channel portion of the sample channel or separation channel.

18. The method of claim 11 wherein the sample chamber is selected from one of the following: a diamond shape, a circular shape or a curve shape.

19. The method of claim 18 wherein a portion of the buffer or separation channels is defined with a reduced cross-sectional area relative to the width of a sample loading channel portion of the sample channel.

20. The method of claim 15 further comprising performing electrophoresis on the injected sample in the separation channel.

* * * * *